US008620397B2

(12) United States Patent
Sterling et al.

(10) Patent No.: US 8,620,397 B2
(45) Date of Patent: *Dec. 31, 2013

(54) METHOD AND APPARATUS FOR DETERMINING AN ANALYTE CONCENTRATION IN A SAMPLE HAVING INTERFERENTS

(75) Inventors: Bernhard B. Sterling, Danville, CA (US); W. Dale Hall, Oakland, CA (US); Kenneth G. Witte, San Jose, CA (US); Mark Wechsler, San Mateo, CA (US); Peng Zheng, Alameda, CA (US); Richard Keenan, Livermore, CA (US)

(73) Assignee: OptiScan Biomedical Corporation, Hayward, CA (US)

( * ) Notice: Subject to any disclaimer, the term of this patent is extended or adjusted under 35 U.S.C. 154(b) by 929 days.

This patent is subject to a terminal disclaimer.

(21) Appl. No.: 12/573,821

(22) Filed: Oct. 5, 2009

(65) Prior Publication Data

US 2010/0221762 A1 Sep. 2, 2010

Related U.S. Application Data

(63) Continuation of application No. 12/140,175, filed on Jun. 16, 2008, now abandoned, which is a continuation of application No. 11/256,656, filed on Oct. 21, 2005, now Pat. No. 7,388,202.

(60) Provisional application No. 60/652,660, filed on Feb. 14, 2005, provisional application No. 60/724,199, filed on Oct. 6, 2005, provisional application No. 60/621,281, filed on Oct. 21, 2004.

(51) Int. Cl.
*A61B 5/1455* (2006.01)
*G01N 21/00* (2006.01)

(52) U.S. Cl.
USPC ................................ 600/322; 422/82.05

(58) Field of Classification Search
USPC .............. 600/309, 310, 322; 422/68.1, 82.05, 422/82.06
See application file for complete search history.

(56) References Cited

U.S. PATENT DOCUMENTS 2,797,149 A 6/1957 Skeggs
3,634,039 A 1/1972 Brondy
(Continued)

FOREIGN PATENT DOCUMENTS

WO WO 02/43866 6/2002
WO WO 03/016882 2/2003
(Continued)

OTHER PUBLICATIONS

International Preliminary Report on Patentability for International Application No. PCT/US2005/037606, dated May 3, 2007.

(Continued)

*Primary Examiner* — Eric Winakur
(74) *Attorney, Agent, or Firm* — Knobbe Martens Olson & Bear LLP

(57) ABSTRACT

A method and apparatus are described that permit an analyte concentration to be estimated from a measurement in the presence of compounds that interfere with the measurement. The method reduces the error in the analyte concentration in the presence of interferents. The method includes the use of a set of measurements obtained for a large population having a range of known analyte and interfering compound concentrations. From a sample measurement, which may or may not be one of the population, likely present interferents are identified, and a calibration vector is calculated.

27 Claims, 22 Drawing Sheets

(56) References Cited

U.S. PATENT DOCUMENTS

| | | | |
|---|---|---|---|
| 4,151,845 A | 5/1979 | Clemens | |
| 4,368,980 A | 1/1983 | Aldred et al. | |
| 4,573,968 A | 3/1986 | Parker | |
| 4,627,014 A | 12/1986 | Lo et al. | |
| 4,657,529 A | 4/1987 | Prince et al. | |
| 4,919,596 A | 4/1990 | Slate et al. | |
| 4,975,581 A | 12/1990 | Robinson et al. | |
| 4,976,270 A | 12/1990 | Parl et al. | |
| 5,134,079 A | 7/1992 | Cusack et al. | |
| 5,165,406 A | 11/1992 | Wong | |
| 5,308,982 A | 5/1994 | Ivaldi et al. | |
| 5,377,674 A | 1/1995 | Kuestner | |
| 5,380,665 A | 1/1995 | Cusack et al. | |
| 5,697,366 A | 12/1997 | Kimball et al. | |
| 5,697,899 A | 12/1997 | Hillman et al. | |
| 5,758,643 A | 6/1998 | Wong et al. | |
| 5,817,007 A | 10/1998 | Fodgaard et al. | |
| 5,902,253 A | 5/1999 | Pfeiffer et al. | |
| 6,017,318 A | 1/2000 | Gauthier et al. | |
| 6,040,578 A | 3/2000 | Malin | |
| 6,101,406 A | 8/2000 | Hacker et al. | |
| 6,115,673 A | 9/2000 | Malin et al. | |
| 6,157,041 A | 12/2000 | Thomas et al. | |
| 6,181,417 B1 | 1/2001 | Dosmann | |
| 6,196,046 B1 | 3/2001 | Braig et al. | |
| 6,200,287 B1 | 3/2001 | Keller et al. | |
| 6,226,082 B1 | 5/2001 | Roe | |
| 6,262,798 B1 | 7/2001 | Shepherd et al. | |
| 6,280,381 B1 | 8/2001 | Malin et al. | |
| 6,285,448 B1 | 9/2001 | Kuenstner | |
| 6,470,279 B1 | 10/2002 | Samsoondar | |
| 6,678,542 B2 | 1/2004 | Braig et al. | |
| 6,697,654 B2 * | 2/2004 | Lorenz et al. | 600/310 |
| 6,862,534 B2 | 3/2005 | Sterling et al. | |
| 6,958,809 B2 | 10/2005 | Sterling et al. | |
| 7,009,180 B2 | 3/2006 | Sterling et al. | |
| 7,050,157 B2 | 5/2006 | Braig et al. | |
| 7,096,124 B2 | 8/2006 | Sterling et al. | |
| 7,115,205 B2 | 10/2006 | Robinson et al. | |
| 7,271,912 B2 | 9/2007 | Sterling et al. | |
| 7,388,202 B2 | 6/2008 | Sterling et al. | |
| 7,593,108 B2 | 9/2009 | Sterling et al. | |
| 7,608,042 B2 * | 10/2009 | Goldberger et al. | 600/309 |
| 2001/0021803 A1 | 9/2001 | Blank et al. | |
| 2002/0010401 A1 | 1/2002 | Bushmakin et al. | |
| 2003/0023148 A1 | 1/2003 | Lorenz et al. | |
| 2003/0086074 A1 | 5/2003 | Braig et al. | |
| 2003/0086075 A1 | 5/2003 | Braig et al. | |
| 2003/0090649 A1 | 5/2003 | Sterling et al. | |
| 2003/0100040 A1 | 5/2003 | Bonnecaze et al. | |
| 2003/0216627 A1 | 11/2003 | Lorenz et al. | |
| 2004/0064259 A1 | 4/2004 | Haaland et al. | |
| 2004/0127777 A1 | 7/2004 | Ruchti et al. | |
| 2004/0147034 A1 | 7/2004 | Gore et al. | |
| 2004/0204868 A1 | 10/2004 | Maynard et al. | |
| 2004/0241736 A1 | 12/2004 | Hendee et al. | |
| 2004/0249308 A1 | 12/2004 | Forssell | |
| 2005/0027463 A1 | 2/2005 | Goode et al. | |
| 2005/0203360 A1 | 9/2005 | Brauker et al. | |
| 2005/0261560 A1 | 11/2005 | Ridder et al. | |
| 2006/0009727 A1 | 1/2006 | O'Mahony et al. | |
| 2006/0079809 A1 | 4/2006 | Goldberger et al. | |
| 2006/0167350 A1 | 7/2006 | Monfre et al. | |
| 2006/0189925 A1 | 8/2006 | Gable et al. | |
| 2006/0200070 A1 | 9/2006 | Callicoat et al. | |
| 2006/0229531 A1 | 10/2006 | Goldberger et al. | |
| 2007/0060872 A1 | 3/2007 | Hall et al. | |
| 2007/0142720 A1 | 6/2007 | Ridder et al. | |
| 2007/0179435 A1 | 8/2007 | Braig et al. | |
| 2007/0191716 A1 | 8/2007 | Goldberger et al. | |
| 2007/0225675 A1 | 9/2007 | Robinson et al. | |
| 2009/0045342 A1 | 2/2009 | Sterling et al. | |
| 2009/0131861 A1 | 5/2009 | Braig et al. | |

FOREIGN PATENT DOCUMENTS

| | | |
|---|---|---|
| WO | WO 2004/092715 A1 | 10/2004 |
| WO | WO 2005/110601 A1 | 11/2005 |
| WO | WO 2006/039310 | 4/2006 |

OTHER PUBLICATIONS

Vonach et al., "Application of Mid-Infrared Transmission Spectrometry to the Direct Determination of Glucose in Whole Blood," Applied Spectroscopy, vol. 52, No. 6, 1998, pp. 820-822.

Hendee, S. et al., "Technical Feasibility of Using Nir Spectroscopy for Continuous Blood Glucose Monitoring"; 2005, in 2 pages.

Berger, Andrew J., et al., "An Enhanced Algorithm for Linear Multivariate Calibration"; Analytical Chemistry, vol. 70, No. 3, pp. 623-627, Feb. 1, 1998.

Berger, Andrew J., Improved Method of Multivariate Linear Calibration, Chapter 4, Ph.D. Thesis, Measurement of Analytes in Human Serum and Whole Blood Samples by Near-Infrared Raman Spectroscopy, 1998, Massachusetts Institute of Technology, Cambridge, Massachusetts.

International Search Report and Written Opinion for International Application No. PCT/US05/37606, date of mailing May 25, 2006.

Billman et. al.,"Clinical Performance of an in line Ex-Vivo Point of Care Monitor: A Multicenter Study," Clinical Chemistry 48:11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkleman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, 1978.

R. Anthony Shaw, et al., "Infrared Spectroscopy in Clinical and Diagnostic Analysis," Encyclopedia of Analytical Chemistry, ed. Robert A. Meyers, John Wiley & Sons, Ltd., pp. 1-20, 2000.

* cited by examiner

METHOD AND APPARATUS FOR DETERMINING AN ANALYTE CONCENTRATION IN A SAMPLE HAVING INTERFERENTS

CROSS-REFERENCE TO RELATED APPLICATIONS

This application is a continuation of U.S. patent application Ser. No. 12/140,175, filed Jun. 16, 2008, titled "METHOD AND APPARATUS FOR DETERMINING AN ANALYTE CONCENTRATION IN A SAMPLE HAVING INTERFERENTS," now abandoned, which is a continuation of U.S. patent application Ser. No. 11/256,656, filed Oct. 21, 2005, titled "METHOD AND APPARATUS FOR DETERMINING AN ANALYTE CONCENTRATION IN A SAMPLE HAVING INTERFERENTS" (now U.S. Pat. No. 7,388,202), which claims the benefit under 35 U.S.C. §119(e) of U.S. Provisional Application No. 60/621,281, filed Oct. 21, 2004, titled "DETERMINATION OF INTERFERENT CONTRIBUTIONS IN BLOOD GLUCOSE ANALYSIS USING HYBRID LINEAR ANALYSIS;" U.S. Provisional Application No. 60/652,660, filed Feb. 14, 2005, titled "ANALYTE DETECTION SYSTEM;" and of U.S. Provisional Application No. 60/724,199, filed Oct. 6, 2005, titled "INTENSIVE CARE UNIT BLOOD ANALYSIS SYSTEM AND METHOD." The entire contents of each of the above-listed non-provisional applications and provisional applications are hereby incorporated by reference herein and made part of this specification.

BACKGROUND

1. Field

Certain embodiments disclosed herein relate to a method and apparatus for determining the concentration of an analyte in a sample, and more particularly to a method and system that minimize the error in determining the analyte concentration due to the presence of sample components that interfere with the analyte measurement.

2. Discussion of the Background

Spectroscopic analysis is a powerful technique for determining the presence of one or more analytes in a sample by monitoring the interaction of light with the sample. Examples of spectroscopic measurements include, but are not limited to, the determination of the amount of light transmitted, absorbed, or scattered from a sample at one or more wavelengths. Thus, for example, absorption analysis includes determining the decrease in the intensity of light transmitted through a sample at one or more wavelengths, and then comparing the change in intensity with an absorption model based, for example, on Beer's law.

SUMMARY

One embodiment disclosed herein diminishes the sensitivity of analyte estimation to the presence of interferents, so that, over their range of likely interferent concentrations, the net effect of the interferents on the analyte measurement is reduced below that of the sensitivity to an analyte of interest.

One embodiment includes a method and apparatus for determining an analyte concentration in a sample that may contain interferents. Possible interferents in the sample are determined by analysis of a sample measurement. In another embodiment, a calibration for estimating an analyte concentration in a sample is generated to minimize the error in the estimation due to possible interferents. In another embodiment, the analyte concentration is estimated from a sample measurement, a plurality of Sample Population spectra taken in the absence of interferents, and a library of interferent spectrum.

One embodiment includes a method of estimating the amount of an analyte in a sample from a measurement, where the sample may include one or more interferents that affect the measurement. The method includes determining the presence of possible interferents to the estimation of the analyte concentration, and determining a calibration that reduces errors in the calibration due to the presence of the determined possible interferents.

One embodiment includes a method of spectroscopically identifying an interferent in a material sample. The method includes forming a statistical model of interferent-free spectra, comparing combinations of material sample spectra and interferent spectra corresponding to varying concentrations of the interferent, and identifying the interferent as a possible interferent if any of said combinations are within predetermined bounds.

One embodiment includes a method for estimating the amount of an analyte in a sample from a measurement of the sample. The method includes identifying one or more possible interferents to the measurement of the analyte in the sample, and calculating a calibration that, when applied to the measurement, provides an estimate of the analyte concentration in the sample. The calculation minimizes the error of interferents on the estimated analyte concentration.

One embodiment includes a method of generating an average calibration vector for estimating the amount of an analyte from the spectrum of a sample having one or more identified interferents. The method includes forming a plurality of spectra each including a combination of one of a plurality of interferent-free spectra, each having a known amount of analyte, and the spectrum of random combinations of possible amounts of the one or more interferents; forming a plurality of first subsets of spectra each including a random selection of said plurality of spectra and defining a corresponding second subset of spectra of the plurality of spectra not included in said first subset. For each first subset of spectra, the method further includes generating a calibration vector using the known analyte concentration corresponding to each spectrum, estimating the amount of analyte from each spectrum of said corresponding second subset using the generated calibration vector, and determining a subset-average error between the estimated amount of analyte and the known amount of analyte. The method further includes calculating an average calibration vector from the calibration vector and determined average error from each subset of spectra to minimize the variance of the error obtained by the use of the averaged calibration.

One embodiment includes a method of generating a calibration vector or estimating an analyte where the measurement is a spectrum. In one embodiment, the spectrum is an infrared spectrum, such as a near infrared or a mid infrared spectrum. In another embodiment, the measurement is obtained on a material sample from a person.

One embodiment includes a method to determine a calibration that minimizes errors in the calibration due to the presence of the determined possible interferents.

One embodiment includes a carrier medium carrying one or more computer readable code segments to instruct a processor to implement any one or combination of the methods disclosed herein.

One embodiment comprises a method of estimating the concentration of an analyte in a sample from a measurement, where the sample may include one or more interferents that affect the measurement. The method comprises determining the presence in the sample of possible interferents to the measurement, and determining a calibration that reduces errors in the measurement due to the presence of the determined possible interferents. The method can further comprise applying the calibration to the measurement, and estimating the analyte concentration based on the calibrated measurement. The measurement can be from a person, wherein the determining the presence of possible interferents and the determining a calibration both include comparing the measurement with population measurements, and where the determining does not require the population to include the person. The measurement can further comprise a spectrum obtained from a material sample, and the spectrum can be an infrared spectrum, a near infrared spectrum or a mid infrared spectrum. The measurement can also further comprise a spectrum obtained from a material sample non-invasively. The material sample can include at least one of the following: blood, a component of blood, interstitial fluid, or urine. The calibration can comprise a vector that is not required to be perpendicular to the spectra of the determined possible interferents. Determining a calibration can minimize errors in the calibration due to the presence of the determined possible interferents.

One embodiment comprises a carrier medium carrying one or more computer readable code segments to instruct a processor to implement a method of estimating the amount of an analyte in a sample from a measurement, where the sample may include one or more interferents that affect the measurement. The method comprises determining the presence in the sample of possible interferents to the measurement, and determining a calibration that reduces errors in the measurement due to the presence of the determined possible interferents. The measurement can comprise a spectrum obtained from a material sample, and the spectrum can be a near infrared spectrum or a mid infrared spectrum. The measurement can also comprise a spectrum obtained from a material sample non-invasively. The material sample can include at least one of the following: blood, a component of blood, interstitial fluid, or urine.

One embodiment comprises a method of spectroscopically identifying an interferent in a material sample. The method comprises forming a statistical model of interferent-free spectra; analyzing combinations of material sample spectra and interferent spectra corresponding to varying concentrations of the interferent; and identifying the interferent as a possible interferent if any of the combinations are within predetermined bounds. Identifying the interferent can include determining the Mahalanobis distance between the combinations of material sample spectra and interferent spectra corresponding to varying concentrations of the interferent and the statistical model of interferent-free spectra. Identifying the interferent can further include determining whether the minimum Mahalanobis distance as a function of interferent concentration is sufficiently small relative to the quantiles of a $\chi^2$ random variable with L degrees of freedom, where L is the number of wavelengths of the spectra.

One embodiment comprises a carrier medium carrying one or more computer readable code segments to instruct a processor to implement a method of spectroscopically identifying an interferent in a material sample. The method comprises forming a statistical model of interferent-free spectra; analyzing combinations of material sample spectra and interferent spectra corresponding to varying concentrations of the interferent; and identifying the interferent as a possible interferent if any of the combinations are within predetermined bounds. Identifying the interferent can include determining the Mahalanobis distance between the combinations of material sample spectra and interferent spectra corresponding to varying concentrations of the interferent and the statistical model of interferent-free spectra. Identifying the interferent can further include determining whether the minimum Mahalanobis distance as a function of interferent concentration is sufficiently small relative to the quantiles of a $\chi^2$ random variable with L degrees of freedom, where L is the number of wavelengths of the spectra.

One embodiment comprises a method for estimating the concentration of an analyte in a sample from a measurement of the sample. The method comprises identifying, based on the measurement, one or more possible interferents to the measurement of the analyte in the sample; calculating a calibration which reduces error attributable to the one or more possible interferents; applying the calibration to the measurement; and estimating, based on the calibrated measurement, the analyte concentration in the sample. The measurement can comprise a spectrum obtained from a material sample, and the spectrum can be a near infrared spectrum or a mid infrared spectrum. The measurement can also comprise a spectrum obtained from a material sample non-invasively. The material sample can include at least one of the following: blood, a component of blood, interstitial fluid, or urine. The analyte can comprise glucose.

One embodiment comprises a carrier medium carrying one or more computer readable code segments to instruct a processor to implement a method for estimating the concentration of an analyte in a sample from a measurement of the sample. The method comprises identifying, based on the measurement, one or more possible interferents to the measurement of the analyte in the sample; calculating a calibration which reduces error attributable to the one or more possible interferents; applying the calibration to the measurement; and estimating, based on the calibrated measurement, the analyte concentration in the sample. The measurement can comprise a spectrum obtained from a material sample, and the spectrum can be a near infrared spectrum or a mid infrared spectrum. The measurement can also comprise a spectrum obtained from a material sample non-invasively. The material sample can include at least one of the following: blood, a component of blood, interstitial fluid, or urine. The analyte can comprise glucose.

One embodiment comprises a method of generating an average calibration vector for estimating the amount of an analyte from the spectrum of a sample having one or more identified interferents. The method comprises forming a plurality of spectra each including a combination of (i) one of a plurality of interferent-free spectra, each such spectrum having an associated known analyte concentration, and (ii) a spectrum derived from random combinations of possible amounts of the one or more interferents. The method further comprises forming a plurality of first subsets of spectra each including a random selection of the plurality of spectra and defining a corresponding second subset of spectra of the plurality of spectra not included in the first subset. The method further comprises, for each first subset of spectra: (a) generating a calibration vector using the known analyte concentration corresponding to each spectrum; (b) estimating the amount of analyte from each spectrum of the corresponding second subset using the generated calibration vector, and (c) determining a subset-average error between the estimated amount of analyte and the known amount of analyte. The method further comprises calculating an average calibration vector from the calibration vector and determined average error from each subset of spectra to minimize the variance of the error obtained by the use of the averaged calibration. In practicing this method, the sample can comprise a material sample, such as blood, plasma, blood component(s), interstitial fluid, or urine. The spectrum of the sample can be obtained non-invasively. The spectrum of the sample can be an infrared spectrum, a mid infrared spectrum, and/or a near infrared spectrum. In one embodiment, the calibration vector is not required to be perpendicular to the spectra of the determined possible interferents. The calibration vector can minimize errors in the calibration due to the presence of the determined possible interferents.

One embodiment comprises a carrier medium carrying one or more computer readable code segments to instruct a processor to implement a method of generating an average calibration vector for estimating the amount of an analyte from the spectrum of a sample having one or more identified interferents. The method comprises forming a plurality of spectra each including a combination of (i) one of a plurality of interferent-free spectra, each such spectrum having an associated known analyte concentration, and (ii) a spectrum derived from random combinations of possible amounts of the one or more interferents. The method further comprises forming a plurality of first subsets of spectra each including a random selection of the plurality of spectra and defining a corresponding second subset of spectra of the plurality of spectra not included in the first subset. The method further comprises, for each first subset of spectra: (a) generating a calibration vector using the known analyte concentration corresponding to each spectrum; (b) estimating the amount of analyte from each spectrum of the corresponding second subset using the generated calibration vector, and (c) determining a subset-average error between the estimated amount of analyte and the known amount of analyte. The method further comprises calculating an average calibration vector from the calibration vector and determined average error from each subset of spectra to minimize the variance of the error obtained by the use of the averaged calibration. In practicing this method, the sample can comprise a material sample, such as blood, plasma, blood component(s), interstitial fluid, or urine. The spectrum of the sample can be obtained non-invasively. The spectrum of the sample can be an infrared spectrum, a mid infrared spectrum, and/or a near infrared spectrum. In one embodiment, the calibration vector is not required to be perpendicular to the spectra of the determined possible interferents. The calibration vector can minimize errors in the calibration due to the presence of the determined possible interferents.

One embodiment comprises an apparatus for estimating the concentration of an analyte in a sample from a measurement, where the sample may include one or more interferents that affect the measurement. The apparatus comprises means for determining the presence in the sample of possible interferents to the measurement, and means for determining a calibration that reduces errors in the measurement due to the presence of the determined possible interferents. The apparatus can further comprise means for applying said calibration to said measurement, and means for estimating said analyte concentration based on said calibrated measurement. The measurement can be from a person, wherein the means for determining the presence of possible interferents and the means for determining a calibration both include means for comparing the measurement with population measurements, and where the determining does not require the population to include the person. The measurement can comprise a spectrum obtained from a material sample, and the spectrum can be an infrared spectrum, a near infrared spectrum or a mid infrared spectrum. The measurement can also comprise a spectrum obtained from a material sample non-invasively. The material sample can include at least one of the following: blood, plasma or other component(s) of blood, interstitial fluid, or urine. The calibration can be a vector that is not required to be perpendicular to the spectra of the determined possible interferents. The means for determining a calibration can minimize errors in the calibration due to the presence of the determined possible interferents.

One embodiment comprises an apparatus for estimating the concentration of an analyte in a sample from a measurement of the sample. The apparatus comprises means for identifying, based on the measurement, one or more possible interferents to the measurement of the analyte in the sample; means for calculating a calibration which reduces error attributable to the one or more possible interferents; means for applying the calibration to the measurement; and means for estimating, based on the calibrated measurement, the analyte concentration in the sample. The measurement can comprise a spectrum obtained from a material sample, and the spectrum can be an infrared spectrum, a near infrared spectrum or a mid infrared spectrum. The measurement can also comprise a spectrum obtained from a material sample non-invasively. The material sample can include at least one of the following: blood, plasma or other component(s) of blood, interstitial fluid, or urine. The analyte can comprise glucose.

One embodiment comprises an analyte detection system. The system comprises a sensor configured to provide information relating to a measurement of an analyte in a sample; a processor; and stored program instructions. The stored program instructions are executable by the processor such that the system: (a) identifies, based on the measurement, one or more possible interferents to the measurement of the analyte in the sample; (b) calculates a calibration which reduces error attributable to the one or more possible interferents; (c) applies the calibration to the measurement; and (d) estimates, based on the calibrated measurement, the analyte concentration in the sample.

One embodiment comprises an analyte detection system. The system comprises a sensor configured to collect information useful for making a measurement of an analyte in a sample; a processor; and software. The software is executable by the processor such that the system determines the presence in the sample of possible interferents to the measurement; and determines a calibration that reduces errors in the measurement due to the presence of the determined possible interferents.

One embodiment comprises an apparatus for analyzing a material sample. The apparatus comprises an analyte detection system; and a sample element configured for operative engagement with the analyte detection system. The sample element comprises a sample chamber having an internal volume for containing a material sample. The analyte detection system includes a processor and stored program instructions. The program instructions are executable by the processor such that, when the material sample is positioned in the sample chamber and the sample element is operatively engaged with the analyte detection system, the system computes estimated concentrations of the analyte in the material sample in the presence of possible interferents to the estimation of the analyte concentration by determining the presence of possible interferents to the estimation of the analyte concentration and determining a calibration that reduces errors in the estimation due to the presence of the determined possible interferents.

Figure 1:
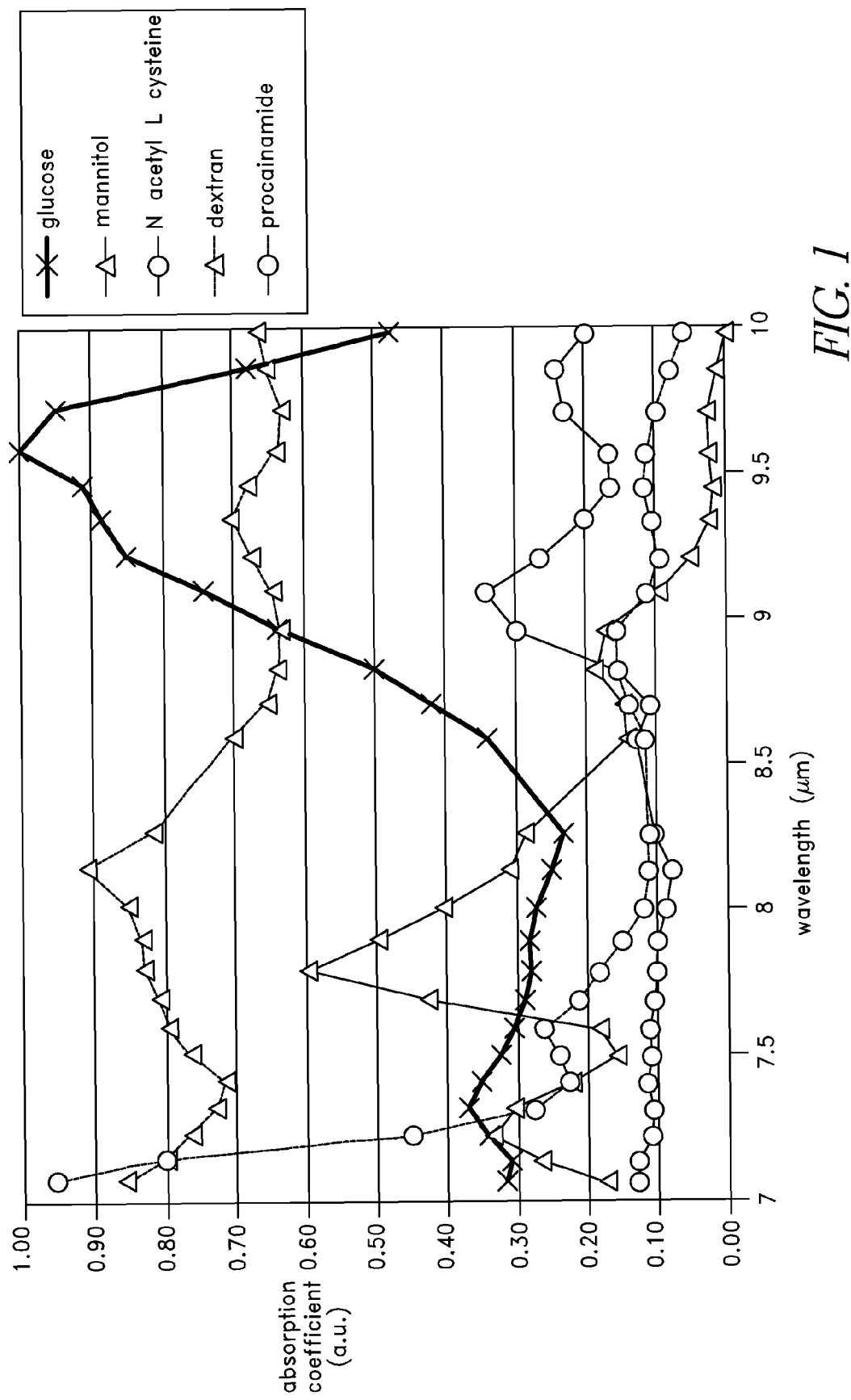
FIG. 1 is a graph illustrating the absorption spectra of various components that may be present in a blood sample.

Reference symbols are used in the Figures to indicate certain components, aspects or features shown therein, with reference symbols common to more than one Figure indicating like components, aspects or features shown therein.

DETAILED DESCRIPTION OF PREFERRED EMBODIMENTS

Although certain embodiments and examples are disclosed below, it will be understood by those skilled in the art that the inventions disclosed herein extend beyond the specifically disclosed embodiments to other alternative embodiments and/or uses of the inventions and obvious modifications and equivalents thereof. Thus it is intended that the scope of the inventions herein disclosed should not be limited by the particular disclosed embodiments described below. In any method or process disclosed herein, the acts or operations making up the method/process may be performed in any suitable sequence, and are not necessarily limited to any particular disclosed sequence. For purposes of contrasting various embodiments with the prior art, certain aspects and advantages of these embodiments are described where appropriate herein. Of course, it is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Several disclosed embodiments are devices and methods for analyzing material sample measurements and for quantifying one or more analytes in the presence of interferents. Interferents can comprise components of a material sample being analyzed for an analyte, where the presence of the interferent affects the quantification of the analyte. Thus, for example, in the spectroscopic analysis of a sample to determine an analyte concentration, an interferent could be a compound having spectroscopic features that overlap with those of the analyte. The presence of such an interferent can introduce errors in the quantification of the analyte. More specifically, the presence of interferents can affect the sensitivity of a measurement technique to the concentration of analytes of interest in a material sample, especially when the system is calibrated in the absence of, or with an unknown amount of, the interferent.

Independently of or in combination with the attributes of interferents described above, interferents can be classified as being endogenous (i.e., originating within the body) or exogenous (i.e., introduced from or produced outside the body). As example of these classes of interferents, consider the analysis of a blood sample (or a blood component sample or a blood plasma sample) for the analyte glucose. Endogenous interferents include those blood components having origins within the body that affect the quantification of glucose, and may include water, hemoglobin, blood cells, and any other component that naturally occurs in blood. Exogenous interferents include those blood components having origins outside of the body that affect the quantification of glucose, and can include items administered to a person, such as medicaments, drugs, foods or herbs, whether administered orally, intravenously, topically, etc.

Independently of or in combination with the attributes of interferents described above, interferents can comprise components which are possibly but not necessarily present in the sample type under analysis. In the example of analyzing samples of blood or blood plasma drawn from patients who are receiving medical treatment, a medicament such as acetaminophen is possibly, but not necessarily present in this sample type. In contrast, water is necessarily present in such blood or plasma samples.

As used herein, the term "material sample" (or, alternatively, "sample") is a broad term and is used in its ordinary sense and includes, without limitation, any material which is suitable for analysis. For example, a material sample may comprise whole blood, blood components (e.g., plasma or serum), interstitial fluid, intercellular fluid, saliva, urine, sweat and/or other organic or inorganic materials, or derivatives of any of these materials. As a further example, a material sample comprises any of the above samples as sensed non-invasively in the body. For example, absorption, emission, or other type of optical spectra, which may be combined with acoustical measurements, such as obtained using photoacoustic techniques, may be obtained on a finger, ear, eye, or some other body part.

As used herein, the term "analyte" is a broad term and is used in its ordinary sense and includes, without limitation, any chemical species the presence or concentration of which is sought in the material sample by an analyte detection system. For example, the analyte(s) include, but are not limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. As used herein, the term "measurement" is a broad term and is used in its ordinary sense and includes, without limitation, one or more optical, physical, chemical, electrochemical, or photoacoustic measurements.

To facilitate an understanding of the inventions, embodiments are discussed herein where one or more analyte concentrations are obtained using spectroscopic measurements of a sample at wavelengths including one or more wavelengths that are identified with the analyte(s). The embodiments disclosed herein are not meant to limit, except as claimed, the scope of certain disclosed inventions which are directed to the analysis of measurements in general.

As an example, certain disclosed methods are used to quantitatively estimate the concentration of one specific compound (an analyte) in a mixture from a measurement, where the mixture contains compounds (interferents) that affect the measurement. Certain disclosed embodiments are particularly effective if each analyte and interferent component has a characteristic signature in the measurement, and if the measurement is approximately affine (i.e., includes a linear component and an offset) with respect to the concentration of each analyte and interferent. In one embodiment, a method includes a calibration process including an algorithm for estimating a set of coefficients and an offset value that permits the quantitative estimation of an analyte. In another embodiment, there is provided a method for modifying hybrid linear algorithm (HLA) methods to accommodate a random set of interferents, while retaining a high degree of sensitivity to the desired component. The data employed to accommodate the random set of interferents are (a) the signatures of each of the members of the family of potential additional components and (b) the typical quantitative level at which each additional component, if present, is likely to appear.

Thus various alternative embodiments include, but are not limited to, the determination of the presence or concentration of analytes, samples, or interferents other than those disclosed herein, of other spectroscopic measurements, such as Raman scattering, near infrared spectroscopic methods, mid infrared spectroscopic methods, of non-spectroscopic measurements, such as electrochemical measurement, or of combinations of different types of measurements, to measurements of samples that are chemically or physically altered to change the concentration of one or more analytes or interferents, and may include to measurements on calibrating mixtures.

Fluid Sampling/Handling and Analyte Detection Systems

Figure 3:
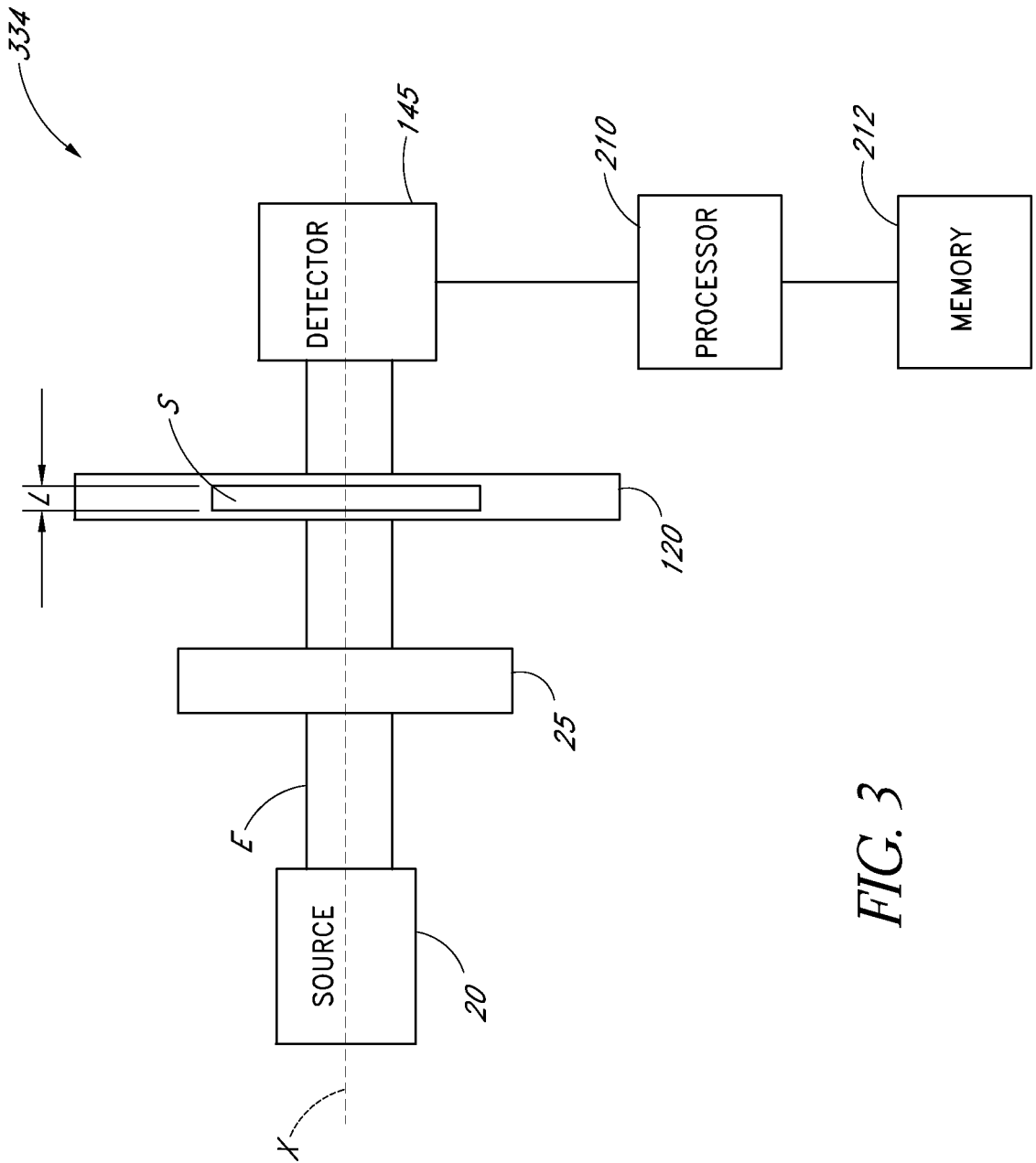
FIG. 3 is one embodiment of an analyte measurement system.
Figure 17:
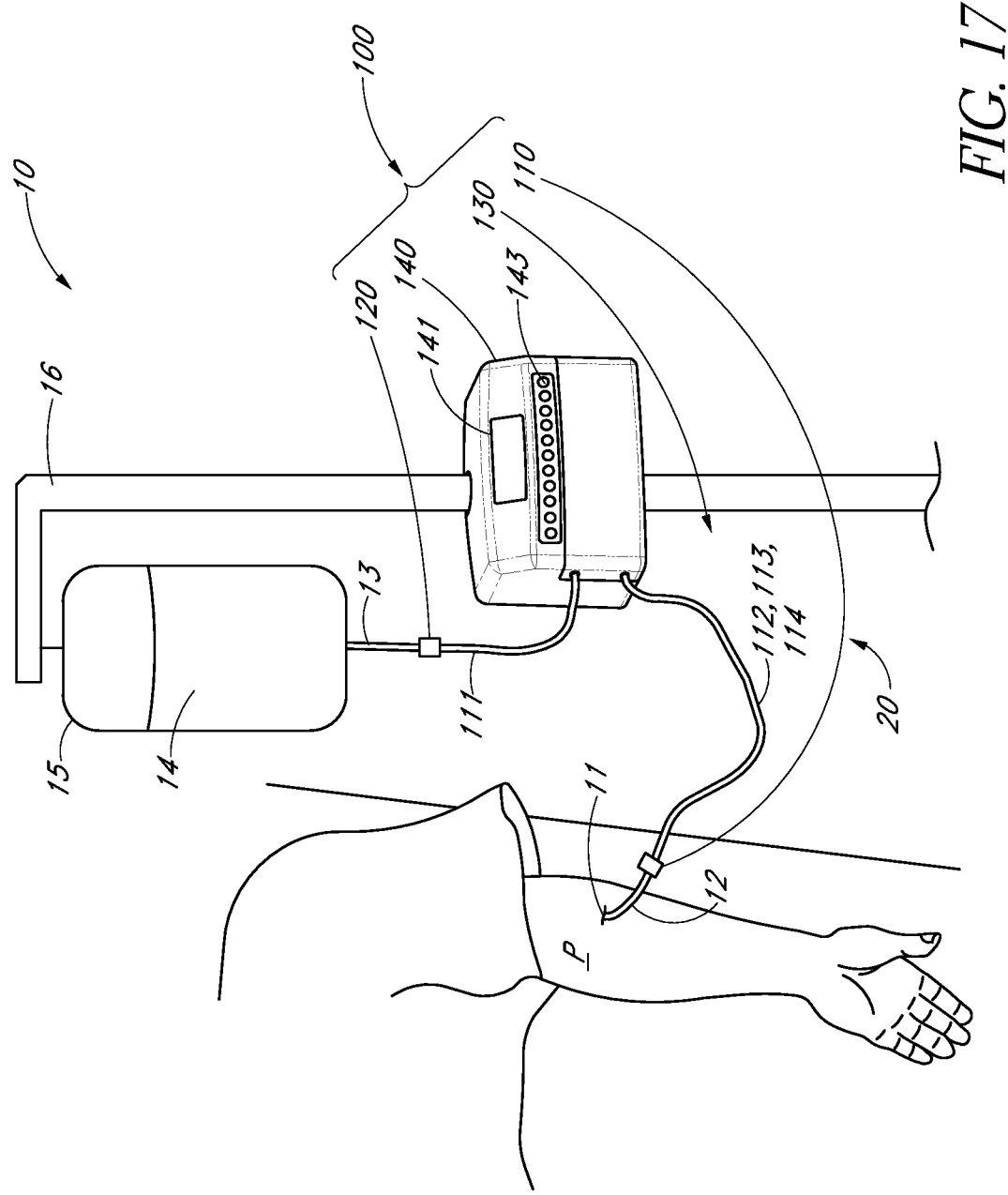
FIG. 17 is a schematic of a fluid handling system.
Figure 18:
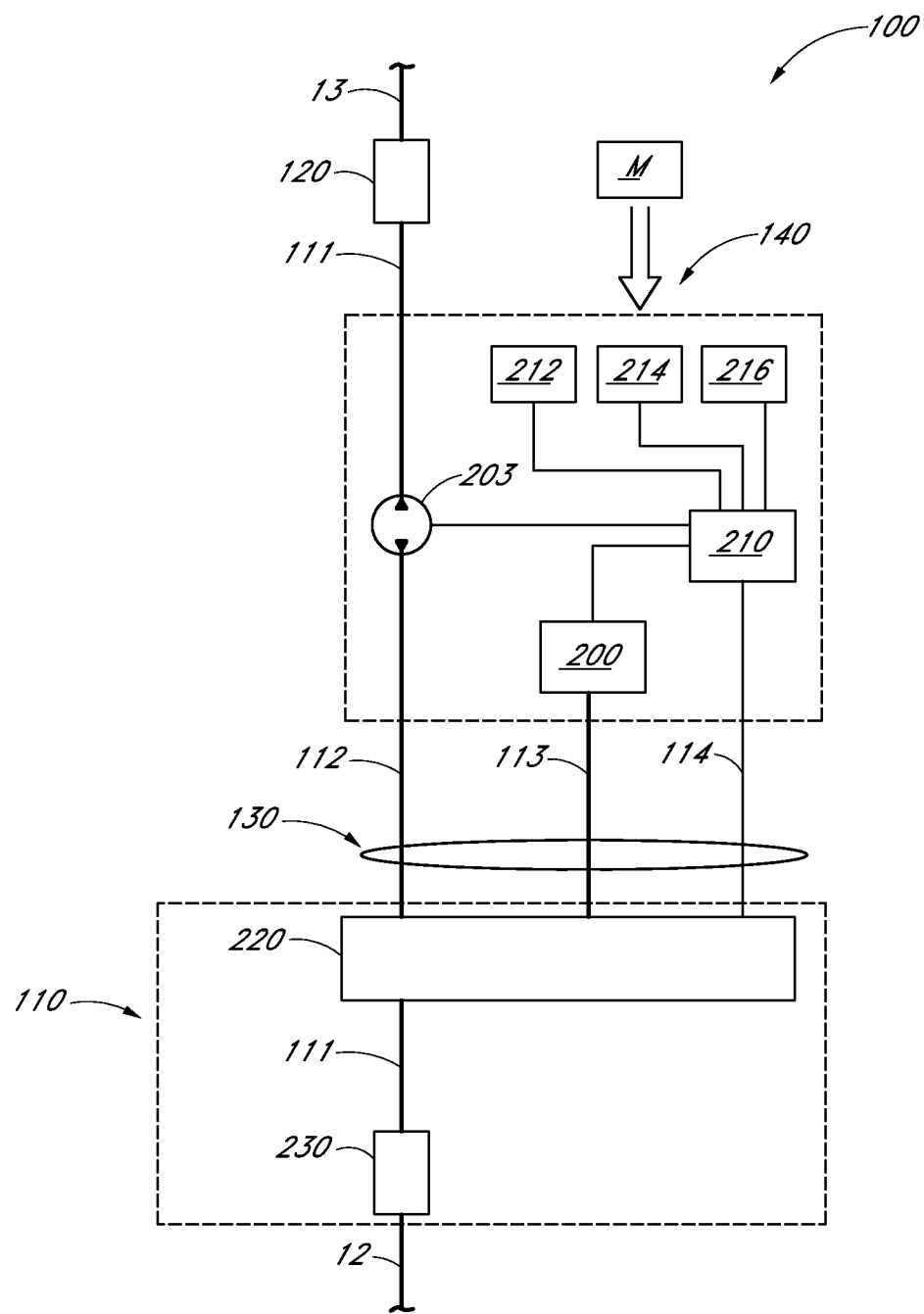
FIG. 18 is a schematic of a first embodiment of a sampling apparatus.
Figure 19:
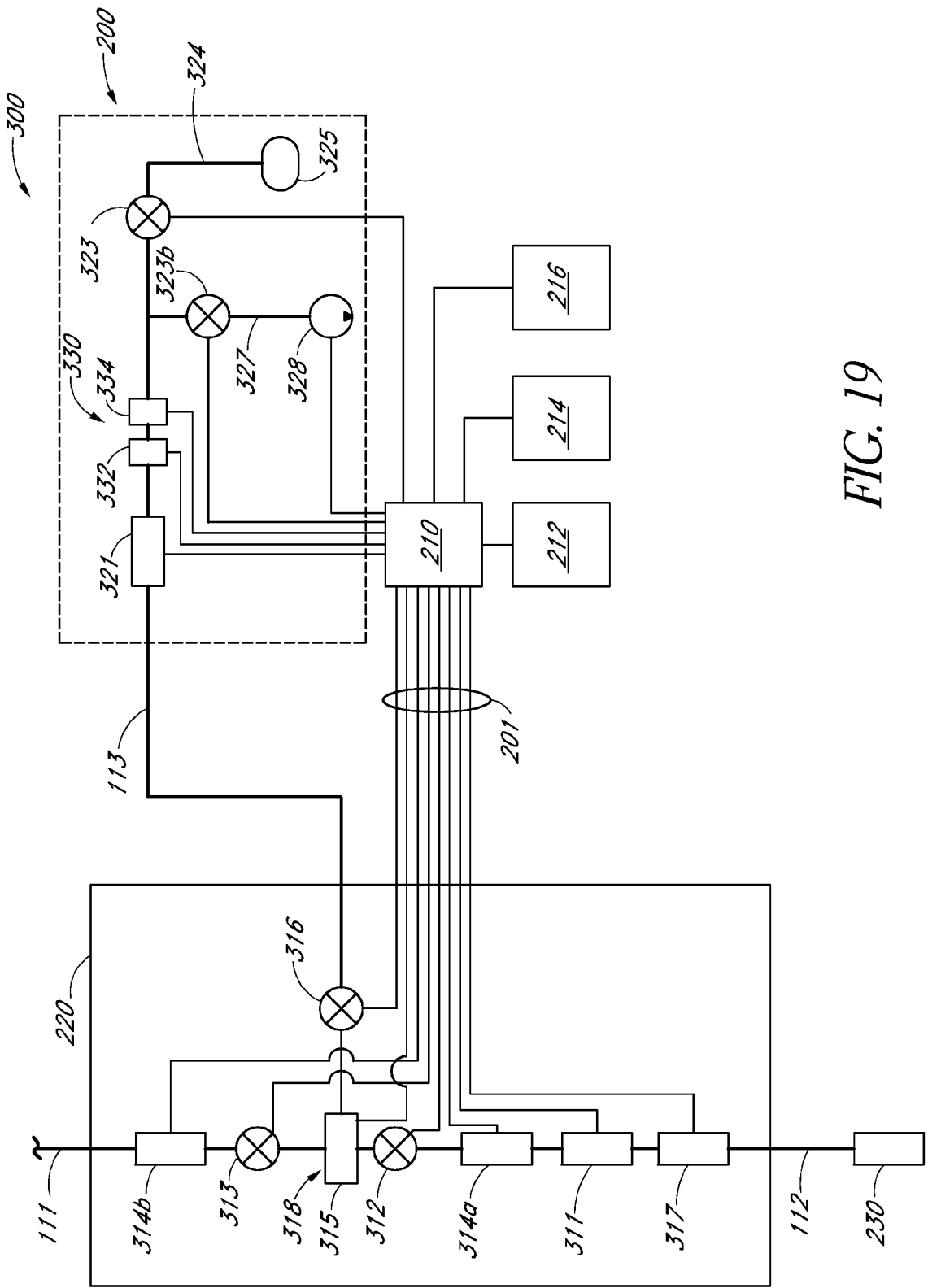
FIG. 19 is a schematic showing details of an embodiment of a sampling apparatus.

Certain methods and devices disclosed herein are directed to the determination of the concentration of one or more analytes from measurements of a material sample that may include interferents. As an illustrative example of such measurements, a system for obtaining optical absorption measurements of blood or plasma samples is discussed with reference to FIGS. 3, 17, 18, and 19, where FIG. 3 depicts one embodiment of an analyte detection system; FIG. 17 is a schematic of a fluid handling system which can be employed to provide material samples to the analyte detection system; FIG. 18 is a schematic of a first embodiment of a sampling apparatus, and FIG. 19 is a schematic showing details of an embodiment of a sampling apparatus.

FIG. 17 is a schematic of one embodiment of a fluid handling system 10. Fluid handling system 10 includes a container 15 supported by a stand 16 and having an interior that is fillable with a fluid 14, a catheter 11, and a sampling system 100. Fluid handling system 10 includes one or more passageways 20 that form conduits between the container, the sampling system, and the catheter. Generally, sampling system 100 is adapted to accept a fluid supply, such as fluid 14, and to be connected to a patient, including, but not limited to catheter 11 which is used to catheterize a patient P. Fluid 14 includes, but is not limited to, fluids for infusing a patient such as saline, lactated Ringer's solution, or water. Sampling system 100, when so connected, is then capable of providing fluid to the patient. In addition, sampling system 100 is also capable of drawing samples, such as blood, from the patient through catheter 11 and passageways 20, and analyzing at least a portion of the drawn sample. Sampling system 100 measures characteristics of the drawn sample including, but not limited to, one or more of the blood plasma glucose, blood urea nitrogen (BUN), hematocrit, hemoglobin, or lactate levels. Optionally, sampling system 100 includes other devices or sensors to measure other patient or apparatus related information including, but not limited to, patient blood pressure, pressure changes within the sampling system, or sample draw rate.

In some embodiments, sampling system 100 includes or is in communication with processors that execute or can be instructed to perform certain methods disclosed herein. Thus, for example, one embodiment of sampling system 100 includes one or more processors (not shown) that are programmed or that are provided with programs to analyze device or sensor measurements to determine analyte measurements from a blood sample from patient P.

More specifically, FIG. 17 shows sampling system 100 as including a patient connector 110, a fluid handling and analysis apparatus 140, and a connector 120. Sampling system 100 may include combinations of passageways, fluid control and measurement devices, and analysis devices to direct, sample, and analyze fluid. Passageways 20 of sampling system 100 include a first passageway 111 from connector 120 to fluid handling and analysis apparatus 140, a second passageway 112 from the fluid handling and analysis apparatus to patient connector 110, and a third passageway 113 from the patient connector to the fluid handling and analysis apparatus. The reference of passageways 20 as including one or more passageway, for example passageways 111, 112, and 113 are provided to facilitate discussion of the system. It is understood that passageways may include one or more separate components and may include other intervening components including, but not limited to, pumps, valves, manifolds, and analytic equipment.

As used herein, the term "passageway" is a broad term and is used in its ordinary sense and includes, without limitation except as explicitly stated, as any opening through a material through which a fluid may pass so as to act as a conduit. Passageways include, but are not limited to, flexible, inflexible or partially flexible tubes, laminated structures having openings, bores through materials, or any other structure that can act as a conduit and any combination or connections thereof. The internal surfaces of passageways that provide fluid to a patient or that are used to transport blood are preferably biocompatible materials, including but not limited to silicone, polyetheretherketone (PEEK), or polyethylene (PE). One type of preferred passageway is a flexible tube having a fluid contacting surface formed from a biocompatible material. A passageway, as used herein, also includes separable portions that, when connected, form a passageway.

The inner passageway surfaces may include coatings of various sorts to enhance certain properties of the conduit, such as coatings that affect the ability of blood to clot or to reduce friction resulting from fluid flow. Coatings include, but are not limited to, molecular or ionic treatments.

As used herein, the term "connector" is a broad term and is used in its ordinary sense and includes, without limitation except as explicitly stated, as a device that connects passageways or electrical wires to provide communication on either side of the connector. Some connectors contemplated herein include a device for connecting any opening through which a fluid may pass. In some embodiments, a connector may also house devices for the measurement, control, and preparation of fluid, as described in several of the embodiments.

Fluid handling and analysis apparatus 140 may control the flow of fluids through passageways 20 and the analysis of samples drawn from a patient P, as described subsequently. Fluid handling and analysis apparatus 140 includes a display 141 and input devices, such as buttons 143. Display 141 provides information on the operation or results of an analysis performed by fluid handling and analysis apparatus 140. In one embodiment, display 141 indicates the function of buttons 143, which are used to input information into fluid handling and analysis apparatus 140. Information that may be input into or obtained by fluid handling and analysis apparatus 140 includes, but is not limited to, a required infusion or dosage rate, sampling rate, or patient specific information which may include, but is not limited to, a patient identification number or medical information. In an other alternative embodiment, fluid handling and analysis apparatus 140 obtains information on patient P over a communications network, for example an hospital communication network having patient specific information which may include, but is not limited to, medical conditions, medications being administered, laboratory blood reports, gender, and weight. As one example of the use of fluid handling system 10, FIG. 17 shows catheter 11 connected to patient P.

As discussed subsequently, fluid handling system 10 may catheterize a patient's vein or artery. Sampling system 100 is releasably connectable to container 15 and catheter 11. Thus, for example, FIG. 17 shows container 15 as including a tube 13 to provide for the passage of fluid to, or from, the container, and catheter 11 as including a tube 12 external to the patient. Connector 120 is adapted to join tube 13 and passageway 111. Patient connector 110 is adapted to join tube 12 and to provide for a connection between passageways 112 and 113.

Patient connector 110 may also include devices that control, direct, process, or otherwise affect the flow through passageways 112 and 113. In some embodiments, one or more control or electrical lines 114 are provided to exchange signals between patient connector 110 and fluid handling and analysis apparatus 140. As shown in FIG. 17, sampling system 100 may also include passageways 112 and 113, and electrical lines 114, when present. The passageways and electrical lines between apparatus 140 and patient connector 110 are referred to, with out limitation, as a bundle 130.

In various embodiments, fluid handling and analysis apparatus 140 and/or patient connector 110, includes other elements (not shown in FIG. 17) that include, but are not limited to: fluid control elements, including but not limited to valves and pumps; fluid sensors, including but not limited to pressure sensors, temperature sensors, hematocrit sensors, hemoglobin sensors, colorimetric sensors, and gas (or "bubble") sensors; fluid conditioning elements, including but not limited to gas injectors, gas filters, and blood plasma separators; and wireless communication devices to permit the transfer of information within the sampling system or between sampling system 100 and a wireless network.

In one embodiment, patient connector 110 includes devices to determine when blood has displaced fluid 14 at the connector end, and thus provides an indication of when a sample is available for being drawn through passageway 113 for sampling. The presence of such a device at patient connector 110 allows for the operation of fluid handling system 10 for analyzing samples without regard to the actual length of tube 12. Accordingly, bundle 130 may include elements to provide fluids, including air, or information communication between patient connector 110 and fluid handling and analysis apparatus 140 including, but not limited to, one or more other passageways and/or wires.

In one embodiment of sampling system 100, the passageways and lines of bundle 130 are sufficiently long to permit locating patient connector 110 near patient P, for example with tube 12 having a length of less than 0.1 to 0.5 meters, or preferably approximately 0.15 meters and with fluid handling and analysis apparatus 140 located at a convenient distance, for example on a nearby stand 16. Thus, for example, bundle 130 is from 0.3 to 3 meters, or more preferably from 1.5 to 2.0 meters in length. It is preferred, though not required, that patient connector 110 and connector 120 include removable connectors adapted for fitting to tubes 12 and 13, respectively. Thus, in one embodiment, container 15/tube 13 and catheter 11/tube 12 are both standard medical components, and sampling system 100 allows for the easy connection and disconnection of one or both of the container and catheter from fluid handling system 10.

In another embodiment of sampling system 100, tubes 12 and 13 and a substantial portion of passageways 111 and 112 have approximately the same internal cross-sectional area. It is preferred, though not required, that the internal cross-sectional area of passageway 113 is less than that of passageways 111 and 112. As described subsequently, the difference in areas permits fluid handling system 10 to transfer a small sample volume of blood from patient connector 110 into fluid handling and analysis apparatus 140.

Thus, for example, in one embodiment passageways 111 and 112 are formed from a tube having an inner diameter from 0.3 millimeter to 1.50 millimeter, or more preferably having a diameter from 0.60 millimeter to 1.2 millimeter. Passageway 113 is formed from a tube having an inner diameter from 0.3 millimeter to 1.5 millimeter, or more preferably having an inner diameter of from 0.6 millimeter to 1.2 millimeter.

While FIG. 17 shows sampling system 100 connecting a patient to a fluid source, the scope of the present disclosure is not meant to be limited to this embodiment. Alternative embodiments include, but are not limited to, a greater or fewer number of connectors or passageways, or the connectors may be located at different locations within fluid handling system 10, and alternate fluid paths. Thus, for example, passageways 111 and 112 may be formed from one tube, or may be formed from two or more coupled tubes including, for example, branches to other tubes within sampling system 100, and/or there may be additional branches for infusing or obtaining samples from a patient. In addition, patient connector 110 and connector 120 and sampling system 100 alternatively include additional pumps and/or valves to control the flow of fluid as described below.

FIG. 18 is a schematic of a sampling system 100 configured to analyze blood from patient P which may be generally similar to the embodiment of the sampling system illustrated in FIG. 17, except as further detailed below. Where possible, similar elements are identified with identical reference numerals in the depiction of the embodiments of FIGS. 17 and 18. FIG. 18 shows patient connector 110 as including a sampling assembly 220 and a connector 230, portions of passageways 111 and 113, and electrical lines 114, and fluid handling and analysis apparatus 140 as including a pump 203, a sampling unit 200, and a controller 210. Passageway 111 provides fluid communication between connector 120 and pump 203 and passageway 113 provides fluid communication between pump 203 and connector 110. As described subsequently in several embodiments, sampling unit 200 may include one or more passageways, pumps and/or valves, and sampling assembly 220 may include passageways, sensors, valves, and/or sample detection devices.

Controller 210 collects information from sensors and devices within sampling assembly 220, from sensors and analytical equipment within sampling unit 200, and provides coordinated signals to control pump 203 and pumps and valves, if present, in sampling assembly 220. Thus, for example, controller 210 is in communication with pump 203, sampling unit 200, and sampling assembly 220 through electrical lines 114.

Controller 210 also has access to memory 212, which may contain some or all of the programming instructions for analyzing measurements from sensors and analytical equipment within sampling unit 200 according to one or more of the methods described herein. Optionally, controller 210 and/or memory 212 has access to a media reader 214 that accepts a media M and/or a communications link 216 to provide programming instructions to accomplish one or more of the methods described herein. Media M includes, but is not limited to, optical media such as a DVD or a CD-ROM. Communications link 216 includes, but is not limited to, a wired or wireless Internet connection.

In some embodiments, controller 210 contains or is provided with programming instructions through memory 212, media reader 214, and/or communications link 216, to perform any one or combination of the methods described herein, including but not limited to the disclosed methods of measurement analysis, interferent determination, and/or calibration constant generation. Alternatively communications link 216 is used to provide measurements from sampling unit 200 for the performance of one or more of the methods described herein.

In other embodiments, communications link 216 establishes a connection to a computer containing patient specific information that may be used by certain methods described herein. Thus, for example, information regarding the patient's medical condition or parameters that affect the determination of analyte concentrations may be transferred from a computer containing patient specific information to memory 212 to aid in the analysis. Examples of such patient specific information include, but are not limited to, current and/or past concentrations of analyte(s) and/or interferent(s) as determined by other analytical equipment.

Fluid handling and analysis apparatus 140 includes the ability to pump in a forward direction (towards the patient) and in a reverse direction (away from the patient). Thus, for example, pump 203 may direct fluid 14 into patient P or draw a sample, such as a blood sample from patient P, from catheter 11 to sampling assembly 220, where it is further directed through passageway 113 to sampling unit 200 for analysis. Preferably, pump 203 provides a forward flow rate at least sufficient to keep the patient vascular line open. In one embodiment, the forward flow rate is from 1 to 5 ml/hr. When operated in a reverse direction, fluid handling and analysis apparatus 140 includes the ability to draw a sample from the patient to sampling assembly 220 and through passageway 113. In one embodiment, pump 203 provides a reverse flow to draw blood to sampling assembly 220, preferably by a sufficient distance past the sampling assembly to ensure that the sampling assembly contains an undiluted blood sample. In one embodiment, passageway 113 has an inside diameter of from 25 to 200 microns, or more preferably from 50 to 100 microns. Sampling unit 200 extracts a small sample, for example from 10 to 100 microliters of blood, or more preferably approximately 40 microliters volume of blood, from sampling assembly 220.

In one embodiment, pump 203 is a directionally controllable pump that acts on a flexible portion of passageway 111. Examples of a single, directionally controllable pump include, but are not limited to a reversible peristaltic pump or two unidirectional pumps that work in concert with valves to provide flow in two directions. In an alternative embodiment, pump 203 includes a combination of pumps, including but not limited to displacement pumps, such as a syringe, and/or valve to provide bi-directional flow control through passageway 111.

Controller 210 includes one or more processors for controlling the operation of fluid handling system 10 and for analyzing sample measurements from fluid handling and analysis apparatus 140. Controller 210 also accepts input from buttons 143 and provides information on display 141. Optionally, controller 210 is in bi-directional communication with a wired or wireless communication system, for example a hospital network for patient information. The one or more processors comprising controller 210 may include one or more processors that are located either within fluid handling and analysis apparatus 140 or that are networked to the unit.

The control of fluid handling system 10 by controller 210 may include, but is not limited to, controlling fluid flow to infuse a patient and to sample, prepare, and analyze samples. The analysis of measurements obtained by fluid handling and analysis apparatus 140 of may include, but is not limited to, analyzing samples based on inputted patient specific information, from information obtained from a database regarding patient specific information, or from information provided over a network to controller 210 used in the analysis of measurements by apparatus 140.

Fluid handling system 10 provides for the infusion and sampling of a patient blood as follows. With fluid handling system 10 connected to bag 15 having fluid 14 and to a patient P, controller 210 infuses a patient by operating pump 203 to direct the fluid into the patient. Thus, for example, in one embodiment, the controller directs that samples be obtained from a patient by operating pump 203 to draw a sample. In one embodiment, pump 203 draws a predetermined sample volume, sufficient to provide a sample to sampling assembly 220. In another embodiment, pump 203 draws a sample until a device within sampling assembly 220 indicates that the sample has reached the patient connector 110. As an example, one such indication is provided by a sensor that detects changes in the color of the sample. Another example is the use of a device that indicates changes in the material within passageway 111 including, but not limited to, a decrease in the amount of fluid 14, a change with time in the amount of fluid, a measure of the amount of hemoglobin, or an indication of a change from fluid to blood in the passageway.

When the sample reaches sampling assembly 220, controller 210 provides an operating signal to valves and/or pumps in sampling system 100 (not shown) to draw the sample from sampling assembly 220 into sampling unit 200. After a sample is drawn towards sampling unit 200, controller 210 then provides signals to pump 203 to resume infusing the patient. In one embodiment, controller 210 provides signals to pump 203 to resume infusing the patient while the sample is being drawn from sampling assembly 220. In an alternative embodiment, controller 210 provides signals to pump 203 to stop infusing the patient while the sample is being drawn from sampling assembly 220. In another alternative embodiment, controller 210 provides signals to pump 203 to slow the drawing of blood from the patient while the sample is being drawn from sampling assembly 220.

In another alternative embodiment, controller 210 monitors indications of obstructions in passageways or catheterized blood vessels during reverse pumping and moderates the pumping rate and/or direction of pump 203 accordingly. Thus, for example, obstructed flow from an obstructed or kinked passageway or of a collapsing or collapsed catheterized blood vessel that is being pumped will result in a lower pressure than an unobstructed flow. In one embodiment, obstructions are monitored using a pressure sensor in sampling assembly 220 or along passageways 20. If the pressure begins to decrease during pumping, or reaches a value that is lower than a predetermined value then controller 210 directs pump 203 to decrease the reverse pumping rate, stop pumping, or pump in the forward direction in an effort to reestablish unobstructed pumping.

FIG. 19 is a schematic showing details of a sampling system 300 which may be generally similar to the embodiments of sampling system 100 as illustrated in FIGS. 17 and 18, except as further detailed below. Sampling system 300 includes sampling assembly 220 having, along passageway 112: connector 230 for connecting to tube 12, a pressure sensor 317, a colorimetric sensor 311, a first bubble sensor 314a, a first valve 312, a second valve 313, and a second bubble sensor 314b. Passageway 113 forms a "T" with passageway 111 at a junction 318 that is positioned between the first valve 312 and second valve 313, and includes a gas injector manifold 315 and a third valve 316. Electrical lines 114 comprise control and/or signal lines extending from colorimetric sensor 311, first, second, and third valves (312, 313, 316), first and second bubble sensors (314a, 314b), gas injector 315, and pressure sensor 317. Sampling system 300 also includes sampling unit 200 which has a bubble sensor 321, a sample analysis device 330, a first valve 323a, a waste receptacle 325, a second valve 323b, and a pump 328. Passageway 113 forms a "T" to form a waste line 324 and a pump line 327.

It is preferred, though not necessary, that the sensors of sampling system 100 are adapted to accept a passageway through which a sample may flow and that sense through the walls of the passageway. As described subsequently, this arrangement allows for the sensors to be reusable and for the passageways to be disposable. It is also preferred, though not necessary, that the passageway is smooth and without abrupt dimensional changes which may damage blood or prevent smooth flow of blood. In addition, is also preferred that the passageways that deliver blood from the patient to the analyzer not contain gaps or size changes that permit fluid to stagnate and not be transported through the passageway.

In one embodiment, the respective passageways on which valves 312, 313, 316, and 323 are situated along passageways that are flexible tubes, and valves 312, 313, 316, and 323 are "pinch valves," in which one or more movable surfaces compress the tube to restrict or stop flow therethrough. In one embodiment, the pinch valves include one or more moving surfaces that are actuated to move together and "pinch" a flexible passageway to stop flow therethrough. Examples of a pinch valve include, for example, Model PV256 Low Power Pinch Valve (Instech Laboratories, Inc., Plymouth Meeting, Pa.). Alternatively, one or more of valves 312, 313, 316, and 323 may be other valves for controlling the flow through their respective passageways.

Colorimetric sensor 311 accepts or forms a portion of passageway 111 and provides an indication of the presence or absence of blood within the passageway. In one embodiment, colorimetric sensor 311 permits controller 210 to differentiate between fluid 14 and blood. Preferably, colorimetric sensor 311 is adapted to receive a tube or other passageway for detecting blood. This permits, for example, a disposable tube to be placed into or through a reusable colorimetric sensor. In an alternative embodiment, colorimetric sensor 311 is located adjacent to bubble sensor 314b. Examples of a colorimetric sensor include, for example, an Optical Blood Leak/Blood vs. Saline Detector available from Introtek International (Edgewood, N.J.).

Sampling system 300 injects a gas—referred to herein and without limitation as a "bubble"—into passageway 113. Specifically, sampling system 300 includes gas injector manifold 315 at or near junction 318 to inject one or more bubbles, each separated by liquid, into passageway 113. The use of bubbles is useful in preventing longitudinal mixing of liquids as they flow through passageways both in the delivery of a sample for analysis with dilution and for cleaning passageways between samples. Thus, for example the fluid in passageway 113 includes, in one embodiment, two volumes of liquids, such as sample S or fluid 14 separated by a bubble, or multiple volumes of liquid each separated by a bubble therebetween.

Bubble sensors 314a, 314b and 321 each accept or form a portion of passageway 112 or 113 and provide an indication of the presence of air, or the change between the flow of a fluid and the flow of air, through the passageway. Examples of bubble sensors include, but are not limited to ultrasonic or optical sensors, that can detect the difference between small bubbles or foam from liquid in the passageway. Once such bubble detector is an MEC Series Air Bubble/Liquid Detection Sensor (Introtek International, Edgewood, N.Y.). Preferably, bubble sensor 314a, 314b, and 321 are each adapted to receive a tube or other passageway for detecting bubbles. This permits, for example, a disposable tube to be placed through a reusable bubble sensor.

Pressure sensor 317 accepts or forms a portion of passageway 111 and provides an indication or measurement of a fluid within the passageway. When all valves between pressure sensor 317 and catheter 11 are open, pressure sensor 317 provides an indication or measurement of the pressure within the patient's catheterized blood vessel. In one embodiment of a method, the output of pressure sensor 317 is provided to controller 210 to regulate the operation of pump 203. Thus, for example, a pressure measured by pressure sensor 317 above a predetermined value is taken as indicative of a properly working system, and a pressure below the predetermined value is taken as indicative of excessive pumping due to, for example, a blocked passageway or blood vessel. Thus, for example, with pump 203 operating to draw blood from patient P, if the pressure as measured by pressure sensor 317 is within a range of normal blood pressures, it may be assumed that blood is being drawn from the patient and pumping continues. However, if the pressure as measured by pressure sensor 317 falls below some level, then controller 210 instructs pump 203 to slow or to be operated in a forward direction to reopen the blood vessel. One such pressure sensor is a Deltran IV part number DPT-412 (Utah Medical Products, Midvale, Utah).

Sample analysis device 330 receives a sample and performs an analysis. In several embodiments, device 330 is configured to prepare the sample for analysis. Thus, for example, device 330 may include a sample preparation unit 332 and an analyte detection system 334, where the sample preparation unit is located between the patient and the analyte detection system. In general, sample preparation occurs between sampling and analysis. Thus, for example, sample preparation unit 332 may take place removed from analyte detection, for example within sampling assembly 220, or may take place adjacent or within analyte detection system 334.

In one embodiment, sample preparation unit 332 removes separates blood plasma from a whole blood sample or removes contaminants from a blood sample and thus comprises one or more devices including, but not limited to, a filter, membrane, centrifuge, or some combination thereof. The preparation of blood plasma permits, for example, an optical measurement to be made with fewer particles, such as blood cells, that might scatter light, and/or provides for the direct determination of analyte concentrations in the plasma. In alternative embodiments, analyte detection system 334 is adapted to analyze the sample directly and sample preparation unit 332 is not required.

Detection system 334 is particularly suited for detecting the concentration of one or more analytes in a material sample S, by detecting energy transmitted through the sample. With reference to FIG. 3, detection system 334 comprises an energy source 20 disposed along a major axis X of the system 334. When activated, the energy source 20 generates an energy beam E which advances from the energy source 20 along the major axis X. Energy beam E passes from source 20, through a sample element or cuvette 120, which supports or contains the material sample S, and then reaches a detector 145. The interaction of energy beam E with sample S occurs over a pathlength L along major axis X. Detector 145 responds to radiation incident thereon by generating an electrical signal and passing the signal to a processor 210 for analysis.

Detection system 334 provides for the measurement of sample S according to the wavelength of energy interacting with sample S. In general, this measurement may be accomplished with beam E of varying wavelengths, or optionally by providing a beam E having a broad range of wavelengths and providing filters between source 20 and detector 145 for selecting a narrower wavelength range for measurement. In one embodiment, the energy source 20 comprises an infrared source and the energy beam E comprises an infrared energy beam, and energy beam E passes through a filter 25, also situated on the major axis X. Based on the signal(s) passed to it by the detector 145, the processor computes the concentration of the analyte(s) of interest in the sample S, and/or the absorbance/transmittance characteristics of the sample S at one or more wavelengths or wavelength bands employed to analyze the sample.

The processor 210 computes the concentration(s), absorbance(s), transmittance(s), etc. by executing a data processing algorithm or program instructions residing within memory 212 accessible by the processor 210. Any one or combination of the methods disclosed herein (including but not limited to the disclosed methods of measurement analysis, interferent determination, and/or calibration constant generation) may be provided to memory 212 or processor 210 via communications with a computer network or by receiving computer readable media (not shown). In addition, any one or combination of the methods disclosed herein may be updated, changed, or otherwise modified by providing new or updated programming, data, computer-readable code, etc. to processor 210.

In one embodiment of analyte detection system 334, filter 25 comprises a varying-passband filter, to facilitate changing, over time and/or during a measurement taken with the detection system 334, the wavelength or wavelength band of the energy beam E that may pass the filter 25 for use in analyzing the sample S. When the energy beam E is filtered with a varying-passband filter, the absorption/transmittance characteristics of the sample S can be analyzed at a number of wavelengths or wavelength bands in a separate, sequential manner. As an example, assume that it is desired to analyze the sample S at N separate wavelengths (Wavelength 1 through Wavelength N). The varying-passband filter is first operated or tuned to permit the energy beam E to pass at Wavelength 1, while substantially blocking the beam E at most or all other wavelengths to which the detector 145 is sensitive (including Wavelengths 2-N). The absorption/transmittance properties of the sample S are then measured at Wavelength 1, based on the beam E that passes through the sample S and reaches the detector 145. The varying-passband filter is then operated or tuned to permit the energy beam E to pass at Wavelength 2, while substantially blocking other wavelengths as discussed above; the sample S is then analyzed at Wavelength 2 as was done at Wavelength 1. This process is repeated until all of the wavelengths of interest have been employed to analyze the sample S. The collected absorption/transmittance data can then be analyzed by the processor 210 to determine the concentration of the analyte(s) of interest in the material sample S. The measured spectrum of sample S is referred to herein in general as $C_s(\lambda_i)$, that is, a wavelength dependent spectrum in which $C_s$ is, for example, a transmittance, an absorbance, an optical density, or some other measure of the optical properties of sample S having values computed or measured at or about each of a number of wavelengths $\lambda_i$, where i ranges over the number of measurements taken. The measurement $C_s(\lambda_i)$ is a linear array of measurements that is alternatively written as $Cs_i$.

The spectral region of analyte detection system 334 depends on the analysis technique and the analyte and mixtures of interest. For example, one useful spectral region for the measurement of glucose concentration in blood or blood plasma using absorption spectroscopy is the mid infrared (for example, about 4 microns to about 11 microns). In an alternative embodiment, glucose concentration is determined using near infrared spectroscopy.

In one embodiment of system 334, energy source 20 produces a beam E having an output in the range of about 4 microns to about 11 microns. Although water is the main contributor to the total absorption across this spectral region, the peaks and other structures present in the blood spectrum from about 6.8 microns to 10.5 microns are due to the absorption spectra of other blood components. The 4 to 11 micron region has been found advantageous because glucose has a strong absorption peak structure from about 8.5 to 10 microns, whereas most other blood constituents have a low and flat absorption spectrum in the 8.5 to 10 micron range. The main exceptions are water and hemoglobin, both of which are interferents in this region.

The amount of spectral detail provided by system 334 depends on the analysis technique and the analyte and mixture of interest. For example, the measurement of glucose in blood by mid-IR absorption spectroscopy can be accomplished with from 11 to 25 filters within a spectral region. In one embodiment of system 334, energy source 20 produces a beam E having an output in the range of about 4 microns to about 11 microns, and filter 25 include a number of narrow band filters within this range, each allowing only energy of a certain wavelength or wavelength band to pass therethrough. Thus, for example, one embodiment filter 25 includes a filter wheel having 11 filters, each having a nominal wavelength approximately equal to one of the following: 3 µm, 4.06 µm, 4.6 µm, 4.9 µm, 5.25 µm, 6.12 µm, 6.47 µm, 7.98 µm, 8.35 µm, 9.65 µm, and 12.2 µm.

Blood samples may be prepared and analyzed by system 334 in a variety of configurations. In one embodiment, sample S is obtained by drawing blood, either using a syringe or as part of a blood flow system, and transferring the blood into cuvette 120. In another embodiment, sample S is drawn into a sample container that is a cuvette 120 adapted for insertion into system 334. In yet another embodiment, sample S is blood plasma that is separated from whole blood by a filter or centrifuge before being placed in cuvette 120.

Measurement Analysis Embodiments

This section discusses a number of computational methods or algorithms which may be used to calculate the concentration of the analyte(s) of interest in the sample S, and/or to compute other measures that may be used in support of calculations of analyte concentrations. Any one or combination of the algorithms disclosed in this section may reside as program instructions stored in the memory 212 so as to be accessible for execution by the processor 210 of the analyte detection system 334 to compute the concentration of the analyte(s) of interest in the sample, or other relevant measures.

Certain methods disclosed herein are directed to the estimation of analyte concentrations in a material sample in the possible presence of an interferent. In certain embodiments, any one or combination of the methods disclosed herein may be accessible and executable processor 210 of system 334. Processor 210 may be connected to a computer network, and data obtained from system 334 can be transmitted over the network to one or more separate computers that implement the methods. The disclosed methods can include the manipulation of data related to sample measurements and other information supplied to the methods (including, but not limited to, interferent spectra, sample population models, and threshold values, as described subsequently). Any or all of this information, as well as specific algorithms, may be updated or changed to improve the method or provide additional information, such as additional analytes or interferents.

Certain disclosed methods generate a "calibration constant" that, when multiplied by a measurement, produces an estimate of an analyte concentration. Both the calibration constant and measurement can comprise arrays of numbers. The calibration constant is calculated to minimize or reduce the sensitivity of the calibration to the presence of interferents that are identified as possibly being present in the sample. Certain methods described herein generate a calibration constant by: 1) identifying the presence of possible interferents; and 2) using information related to the identified interferents to generate the calibration constant. These certain methods do not require that the information related to the interferents includes an estimate of the interferent concentration—they merely require that the interferents be identified as possibly present. In one embodiment, the method uses a set of training spectra each having known analyte concentration(s) and produces a calibration that minimizes the variation in estimated analyte concentration with interferent concentration. The resulting calibration constant is proportional to analyte concentration(s) and, on average, is not responsive to interferent concentrations.

In one embodiment, it is not required (though not prohibited either) that the training spectra include any spectrum from the individual whose analyte concentration is to be determined. That is, the term "training" when used in reference to the disclosed methods does not require training using measurements from the individual whose analyte concentration will be estimated (e.g., by analyzing a bodily fluid sample drawn from the individual).

Several terms are used herein to describe the estimation process. As used herein, the term "Sample Population" is a broad term and includes, without limitation, a large number of samples having measurements that are used in the computation of a calibration—in other words, used to train the method of generating a calibration. For an embodiment involving the spectroscopic determination of glucose concentration, the Sample Population measurements can each include a spectrum (analysis measurement) and a glucose concentration (analyte measurement). In one embodiment, the Sample Population measurements are stored in a database, referred to herein as a "Population Database."

The Sample Population may or may not be derived from measurements of material samples that contain interferents to the measurement of the analyte(s) of interest. One distinction made herein between different interferents is based on whether the interferent is present in both the Sample Population and the sample being measured, or only in the sample. As used herein, the term "Type-A interferent" refers to an interferent that is present in both the Sample Population and in the material sample being measured to determine an analyte concentration. In certain methods it is assumed that the Sample Population includes only interferents that are endogenous, and does not include any exogenous interferents, and thus Type-A interferents are endogenous. The number of Type-A interferents depends on the measurement and analyte(s) of interest, and may number, in general, from zero to a very large number. The material sample being measured, for example sample S, may also include interferents that are not present in the Sample Population. As used herein, the term "Type-B interferent" refers to an interferent that is either: 1) not found in the Sample Population but that is found in the material sample being measured (e.g., an exogenous interferent), or 2) is found naturally in the Sample Population, but is at abnormally high concentrations in the material sample (e.g., an endogenous interferent). Examples of a Type-B exogenous interferent may include medications, and examples of Type-B endogenous interferents may include urea in persons suffering from renal failure. In the example of mid-IR spectroscopic absorption measurement of glucose in blood, water is found in all blood samples, and is thus a Type-A interferent. For a Sample Population made up of individuals who are not taking intravenous drugs, and a material sample taken from a hospital patient who is being administered a selected intravenous drug, the selected drug is a Type-B interferent.

In one embodiment, a list of one or more possible Type-B Interferents is referred to herein as forming a "Library of Interferents," and each interferent in the library is referred to as a "Library Interferent." The Library Interferents include exogenous interferents and endogenous interferents that may be present in a material sample due, for example, to a medical condition causing abnormally high concentrations of the endogenous interferent.

Figure 2:
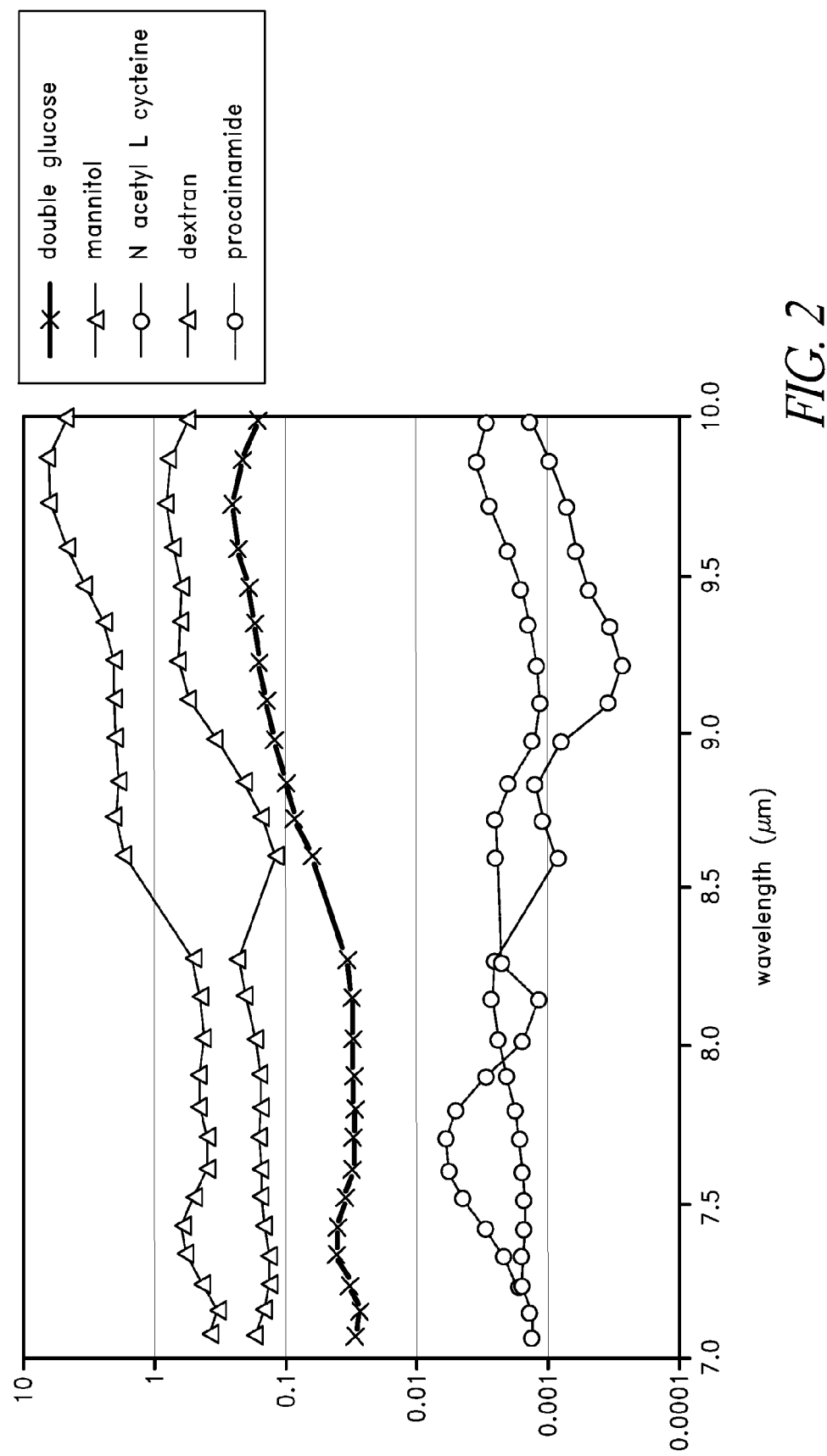
FIG. 2 is a graph illustrating the change in the absorption spectra of blood having the indicated additional components of FIG. 1 relative to a Sample Population blood and glucose concentration, where the contribution due to water has been numerically subtracted from the spectra.

In addition to components naturally found in the blood, the ingestion or injection of some medicines or illicit drugs can result in very high and rapidly changing concentrations of exogenous interferents. This results in problems in measuring analytes in blood of hospital or emergency room patients. An example of overlapping spectra of blood components and medicines is illustrated in FIG. 1 as the absorption coefficient at the same concentration and optical pathlength of pure glucose and three spectral interferents, specifically mannitol (chemical formula: hexane-1,2,3,4,5,6-hexaol), N acetyl L cysteine, dextran, and procainamide (chemical formula: 4-amino-N-(2-diethylaminoethyl)benzamid). FIG. 2 shows the logarithm of the change in absorption spectra from a Sample Population blood composition as a function of wavelength for blood containing additional likely concentrations of components, specifically, twice the glucose concentration of the Sample Population and various amounts of mannitol, N acetyl L cysteine, dextran, and procainamide. The presence of these components is seen to affect absorption over a wide range of wavelengths. It can be appreciated that the determination of the concentration of one species without a priori knowledge or independent measurement of the concentration of other species is problematic.

Figure 4:
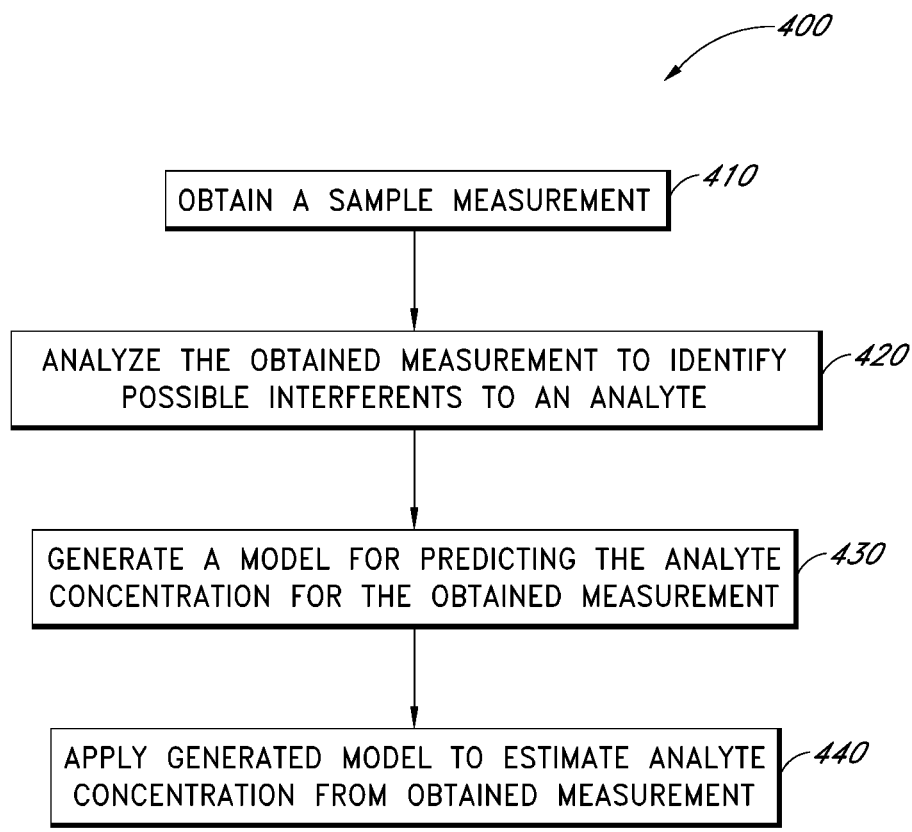
FIG. 4 is a first embodiment of an analysis method for determining the concentration of an analyte in the presence of possible interferents.

One method for estimating the concentration of an analyte in the presence of interferents is presented in flowchart 400 of FIG. 4 as a first step (Block 410) where a measurement of a sample is obtained, a second step (Block 420), where the obtained measurement data is analyzed to identify possible interferents to the analyte, a third step (Block 430) where a model is generated for predicting the analyte concentration in the presence of the identified possible interferents, and a fourth step (Block 440) where the model is used to estimate the analyte concentration in the sample from the measurement. Preferably the step of Block 430 generates a model where the error is minimized for the presence of the identified interferents that are not present in a general population of which the sample is a member.

An embodiment of the method of flowchart 400 for the determination of an analyte from spectroscopic measurements will now be discussed. Further, this embodiment will estimate the amount of glucose concentration in blood sample S, without limit to the scope of the inventions disclosed herein. In one embodiment, the measurement of Block 410 is an absorbance spectrum, $C_s(\lambda_i)$, of a measurement sample S that has, in general, one analyte of interest, glucose, and one or more interferents. In one embodiment, the methods include generating a calibration constant $\kappa(\lambda_i)$ that, when multiplied by the absorbance spectrum $C_s(\lambda_i)$, provides an estimate, $g_{est}$, of the glucose concentration $g_s$.

As described subsequently, one embodiment of Block 420 includes a statistical comparison of the absorbance spectrum of sample S with a spectrum of the Sample Population and combinations of individual Library Interferent spectra. After the analysis of Block 420, a list of Library Interferents that are possibly contained in sample S has been identified and includes, depending on the outcome of the analysis of Block 420, either no Library Interferents, or one or more Library Interferents. Block 430 then generates a large number of spectra using the large number of spectra of the Sample Population and their respective known analyte concentrations and known spectra of the identified Library Interferents. Block 430 then uses the generated spectra to generate a calibration constant matrix to convert a measured spectrum to an analyte concentration that is the least sensitive to the presence of the identified Library Interferents. Block 440 then applies the generated calibration constant to predict the glucose concentration in sample S.

As indicated in Block 410, a measurement of a sample is obtained. For illustrative purposes, the measurement, $C_s(\lambda_i)$, is assumed to be a plurality of measurements at different wavelengths, or analyzed measurements, on a sample indicating the intensity of light that is absorbed by sample S. It is to be understood that spectroscopic measurements and computations may be performed in one or more domains including, but not limited to, the transmittance, absorbance and/or optical density domains. The measurement $C_s(\lambda_i)$ is an absorption, transmittance, optical density or other spectroscopic measurement of the sample at selected wavelength or wavelength bands. Such measurements may be obtained, for example, using analyte detection system 334. In general, sample S contains Type-A interferents, at concentrations preferably within the range of those found in the Sample Population.

In one embodiment, absorbance measurements are converted to pathlength normalized measurements. Thus, for example, the absorbance is converted to optical density by dividing the absorbance by the optical pathlength, L, of the measurement. In one embodiment, the pathlength L is measured from one or more absorption measurements on known compounds. Thus, in one embodiment, one or more measurements of the absorption through a sample S of water or saline solutions of known concentration are made and the pathlength, L, is computed from the resulting absorption measurement(s). In another embodiment, absorption measurements are also obtained at portions of the spectrum that are not appreciably affected by the analytes and interferents, and the analyte measurement is supplemented with an absorption measurement at those wavelengths.

The next step of flowchart 400 is to determine which Library Interferents are present in the sample. In particular, Block 420 indicates that the measurements are analyzed to identify possible interferents. For spectroscopic measurements, it is preferred that the determination is made by comparing the obtained measurement to interferent spectra in the optical density domain. The results of this step provide a list of interferents that may, or are likely to, be present in the sample. In one embodiment, several input parameters are used to estimate a glucose concentration $g_{est}$ from a measured spectrum, $C_s$. The input parameters include previously gathered spectrum measurement of samples that, like the measurement sample, include the analyte and combinations of possible interferents from the interferent library; and spectrum and concentration ranges for each possible interferent. More specifically, the input parameters are:

Library of Interferent Data: Library of Interferent Data includes, for each of "M" interferents, the absorption spectrum of each interferent, $IF=\{IF_1, IF_2, \ldots, IF_M\}$, where $m=1, 2, \ldots, M$; and a maximum concentration for each interferent, $Tmax=\{Tmax_1, Tmax_2, \ldots, Tmax_M\}$; and Sample Population Data: Sample Population Data includes individual spectra of a statistically large population taken over the same wavelength range as the sample spectrum, $Cs_i$, and an analyte concentration corresponding to each spectrum. As an example, if there are N Sample Population spectra, then the spectra can be represented as $C=\{C_1, C_2, \ldots, C_N\}$, where $n=1, 2, \ldots, N$, and the analyte concentration corresponding to each spectrum can be represented as $g=\{g_1, g_2, \ldots, g_N\}$. Preferably, the Sample Population does not have any of the M interferents present, and the material sample has interferents contained in the Sample Population and none or more of the Library Interferents. Stated in terms of Type-A and Type-B interferents, the Sample Population has Type-A interferents and the material sample has Type-A and may have Type-B interferents. The Sample Population Data are used to statistically quantify an expected range of spectra and analyte concentrations. Thus, for example, for a system 10 or 334 used to determine glucose in blood of a person having unknown spectral characteristics, the spectral measurements are preferably obtained from a statistical sample of the population.

Interferent Determination

Figure 5:
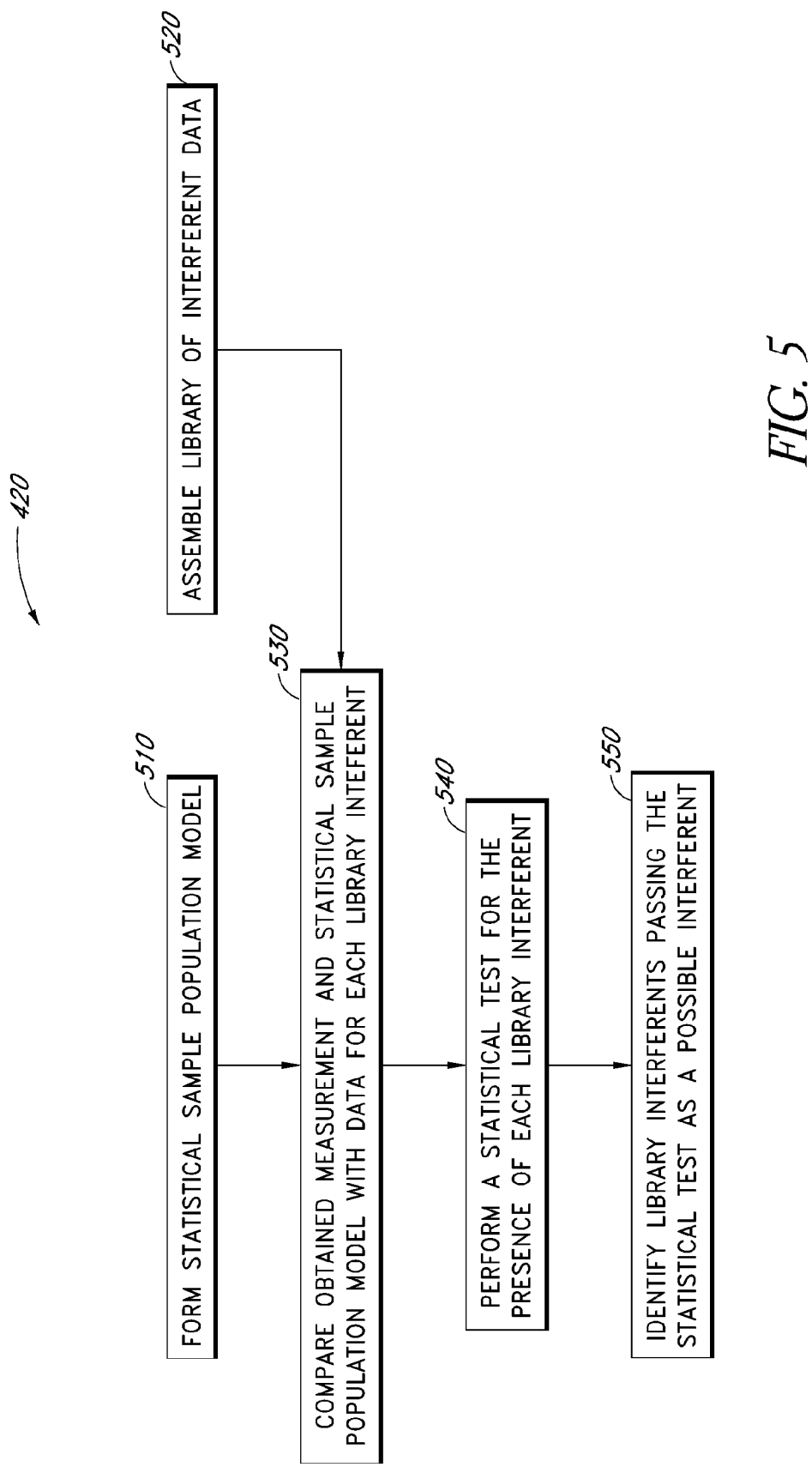
FIG. 5 is one embodiment of a method for identifying interferents in a sample for use with the first embodiment of FIG. 4.

One embodiment of the method of Block 420 is shown in greater detail with reference to the flowchart of FIG. 5. The method includes forming a statistical Sample Population model (Block 510), assembling a library of interferent data (Block 520), comparing the obtained measurement and statistical Sample Population model with data for each interferent from an interferent library (Block 530), performing a statistical test for the presence of each interferent from the interferent library (Block 540), and identifying each interferent passing the statistical test as a possible Library Interferent (Block 550). The steps of Block 520 can be performed once or can be updated as necessary. The steps of Blocks 530, 540, and 550 can either be performed sequentially for all interferents of the library, as shown, or alternatively, be repeated sequentially for each interferent.

One embodiment of each of the methods of Blocks 510, 520, 530, 540, and 550 are now described for the example of identifying Library Interferents in a sample from a spectroscopic measurement using Sample Population Data and a Library of Interferent Data, as discussed previously. Each Sample Population spectrum includes measurements (e.g., of optical density) taken on a sample in the absence of any Library Interferents and has an associated known analyte concentration. A statistical Sample Population model is formed (Block 510) for the range of analyte concentrations by combining all Sample Population spectra to obtain a mean matrix and a covariance matrix for the Sample Population. Thus, for example, if each spectrum at n different wavelengths is represented by an n×1 matrix, C, then the mean spectrum, $\mu$, is a n×1 matrix with the (e.g., optical density) value at each wavelength averaged over the range of spectra, and the covariance matrix, V, is the expected value of the deviation between C and $\mu$ as $V=E((C-\mu)(C-\mu)^T)$. The matrices $\mu$ and V are one model that describes the statistical distribution of the Sample Population spectra.

In another step, Library Interferent information is assembled (Block 520). A number of possible interferents are identified, for example as a list of possible medications or foods that might be ingested by the population of patients at issue or measured by system 10 or 334, and their spectra (in the absorbance, optical density, or transmission domains) are obtained. In addition, a range of expected interferent concentrations in the blood, or other expected sample material, are estimated. Thus, each of M interferents has spectrum IF and maximum concentration Tmax. This information is preferably assembled once and is accessed as needed.

The obtained measurement data and statistical Sample Population model are next compared with data for each interferent from the interferent library (Block 530) to perform a statistical test (Block 540) to determine the identity of any interferent in the mixture (Block 550). This interferent test will first be shown in a rigorous mathematical formulation, followed by a discussion of FIGS. 6A and 6B which illustrates the method.

Mathematically, the test of the presence of an interferent in a measurement proceeds as follows. The measured optical density spectrum, $C_s$ is modified for each interferent of the library by analytically subtracting the effect of the interferent, if present, on the measured spectrum. More specifically, the measured optical density spectrum, $C_s$ is modified, wavelength-by-wavelength, by subtracting an interferent optical density spectrum. For an interferent, M, having an absorption spectrum per unit of interferent concentration, $IF_M$, a modified spectrum is given by $C'_s(T)=C_s-IF_M T$, where T is the interferent concentration, which ranges from a minimum value, Tmin, to a maximum value Tmax. The value of Tmin may be zero or, alternatively, be a value between zero and Tmax, such as some fraction of Tmax.

Next, the Mahalanobis distance (MD) between the modified spectrum $C'_s(T)$ and the statistical model ($\mu$, V) of the Sample Population spectra is calculated as:

$$MD^2(C_s-(Tt),\mu;\rho\rho_s)=(C_s-(TIF_m)-\mu)^T V^{-1}(C_s-(TIF_m)-\mu) \qquad \text{Eq. (1)}$$

The test for the presence of interferent IF is to vary T from Tmin to Tmax (i.e., evaluate $C'_s(T)$ over a range of values of T) and determine whether the minimum MD in this interval is in a predetermined range. Thus for example, one could determine whether the minimum MD in the interval is sufficiently small relative to the quantiles of $\chi^2$ random variable with L degrees of freedom (L=number of wavelengths).

Figure 6A:
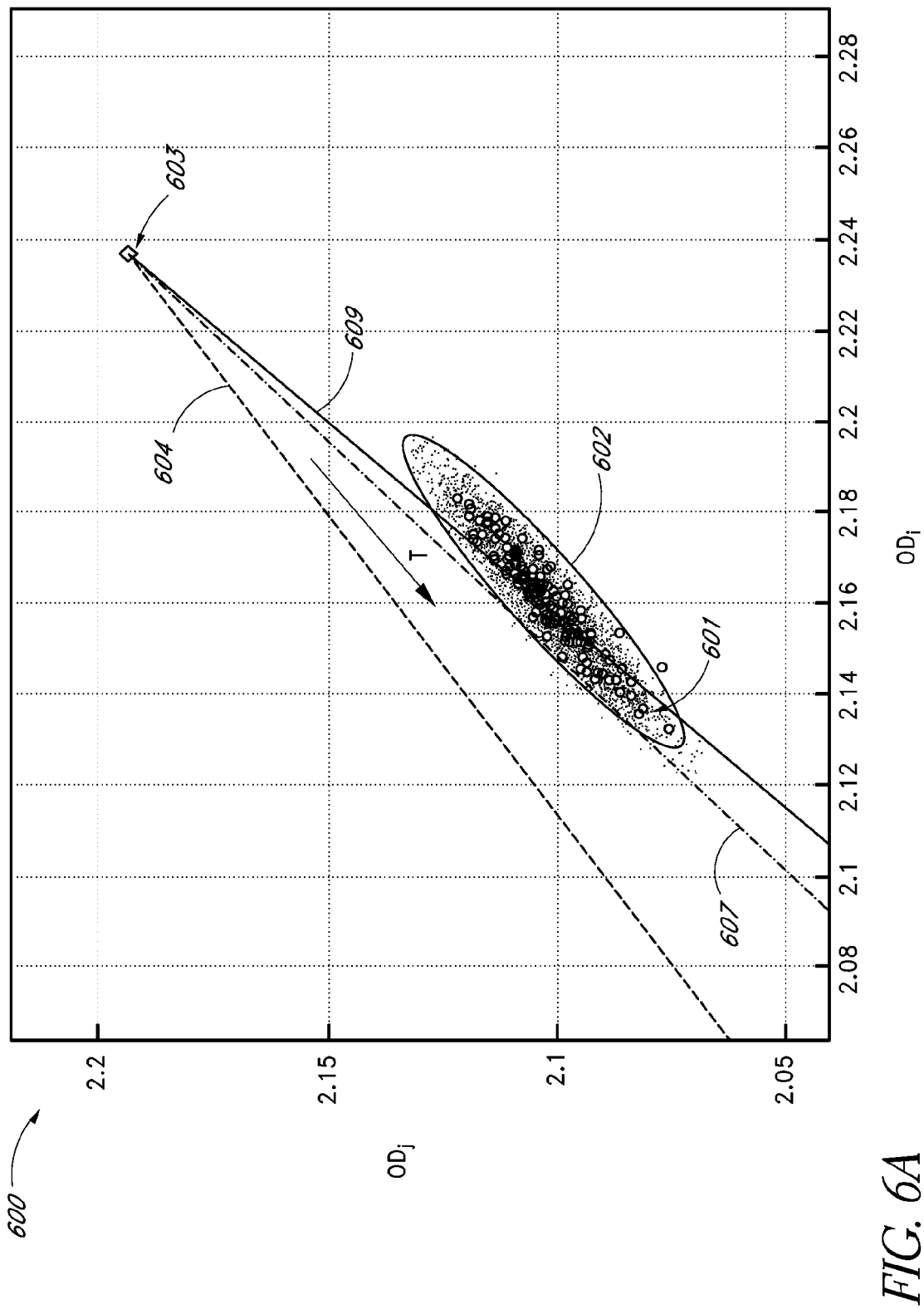
FIG. 6A is a graph illustrating one embodiment of the method of FIG. 5.

FIG. 6A is a graph 600 illustrating the steps of Blocks 530 and 540. The axes of graph 600, $OD_i$ and $OD_j$, are used to plot optical densities at two of the many wavelengths at which measurements are obtained. The points 601 are the measurements in the Sample Population distribution. Points 601 are clustered within an ellipse that has been drawn to encircle the majority of points. Points 601 inside ellipse 602 represent measurements in the absence of Library Interferents. Point 603 is the sample measurement. Presumably, point 603 is outside of the spread of points 601 due the presence of one or more Library Interferents. Lines 604, 607, and 609 indicate the measurement of point 603 as corrected for increasing concentration, T, of three different Library Interferents over the range from Tmin to Tmax. The three interferents of this example are referred to as interferent #1, interferent #2, and interferent #3. Specifically, lines 604, 607, and 609 are obtained by subtracting from the sample measurement an amount T of a Library Interferent (interferent #1, interferent #2, and interferent #3, respectively), and plotting the corrected sample measurement for increasing T.

Figure 6B:
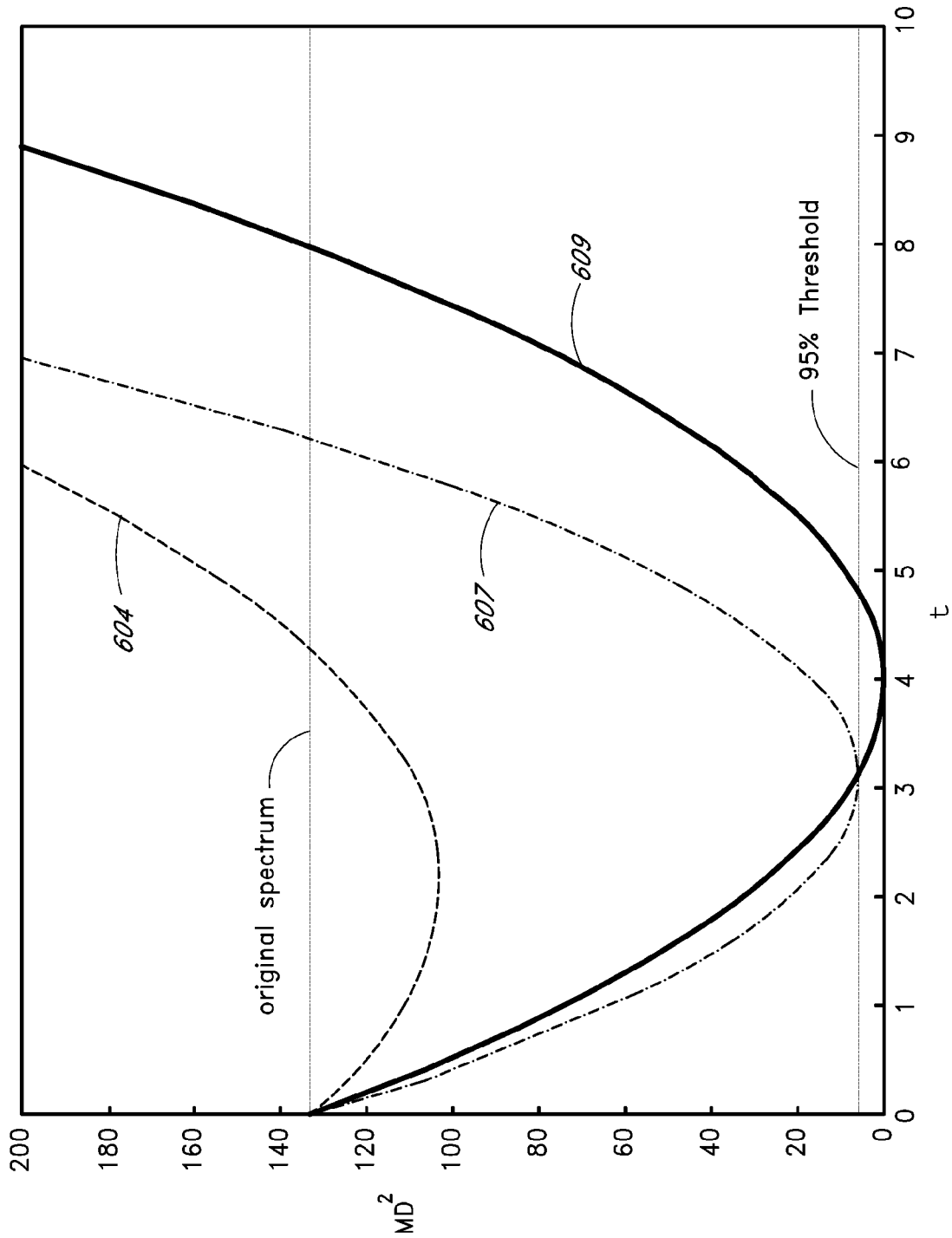
FIG. 6B is a graph further illustrating the method of FIG. 5.

FIG. 6B is a graph further illustrating the method of FIG. 5. In the graph of FIG. 6B, the squared Mahalanobis distance, $MD^2$ has been calculated and plotted as a function of t for lines 604, 607, and 609. Referring to FIG. 6A, line 604 reflects decreasing concentrations of interferent #1 and only slightly approaches points 601. The value of $MD^2$ of line 604, as shown in FIG. 6B, decreases slightly and then increases with decreasing interferent #1 concentration.

Referring to FIG. 6A, line 607 reflects decreasing concentrations of interferent #2 and approaches or passes through many points 601. The value of $MD^2$ of line 607, as shown in FIG. 6B, shows a large decrease at some interferent #2 concentration, then increases. Referring to FIG. 6A, line 609 has decreasing concentrations of interferent #3 and approaches or passes through even more points 3303. The value of $MD^2$ of line 609, as shown in FIG. 6B, shows a still larger decrease at some interferent #3 concentration.

In one embodiment, a threshold level of $MD^2$ is set as an indication of the presence of a particular interferent. Thus, for example, FIG. 6B shows a line labeled "original spectrum" indicating $MD^2$ when no interferents are subtracted from the spectrum, and a line labeled "95% Threshold", indicating the 95% quantile for the $chi^2$ distribution with L degrees of freedom (where L is the number of wavelengths represented in the spectra). This level is the value which should exceed 95% of the values of the $MD^2$ metric; in other words, values at this level are uncommon, and those far above it should be quite rare. Of the three interferents represented in FIGS. 6A and 6B, only interferent #3 has a value of $MD^2$ below the threshold. Thus, this analysis of the sample indicates that interferent #3 is the most likely interferent present in the sample. Interferent #1 has its minimum far above the threshold level and is extremely unlikely to be present; interferent #2 barely crosses the threshold, making its presence more likely than interferent #1, but still far less likely to be present than interferent #1.

As described subsequently, information related to the identified interferents is used in generating a calibration constant that is relatively insensitive to a likely range of concentration of the identified interferents. In addition to being used in certain methods described subsequently, the identification of the interferents may be of interest and may be provided in a manner that would be useful. Thus, for example, for a hospital based glucose monitor, identified interferents may be reported on display 141 or be transmitted to a hospital computer via communications link 216.

Calibration Constant Generation Embodiments

Figure 7:
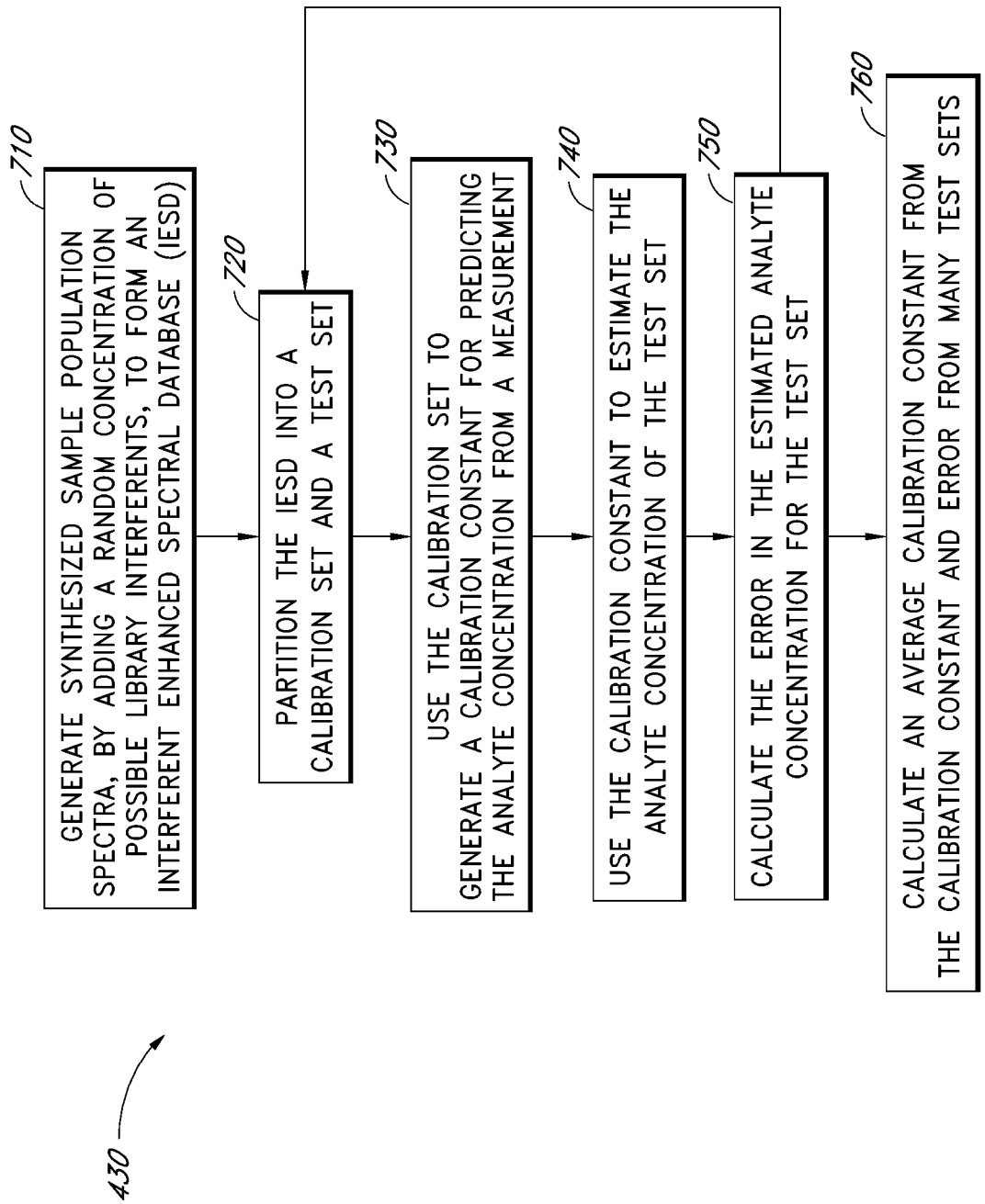
FIG. 7 is a one embodiment of a method for generating a model for identifying possible interferents in a sample for use with the first embodiment of FIG. 4.

Once Library Interferents are identified as being possibly present in the sample under analysis, a calibration constant for estimating the concentration of analytes in the presence of the identified interferents is generated (Block 430). More specifically, after Block 420, a list of possible Library Interferents is identified as being present. One embodiment of the steps of Block 420 are shown in the flowchart of FIG. 7 as Block 710, where synthesized Sample Population measurements are generated, Block 720, where the synthesized Sample Population measurements are partitioned in to calibration and test sets, Block 730, where the calibration are is used to generate a calibration constant, Block 740, where the calibration set is used to estimate the analyte concentration of the test set, Block 750 where the errors in the estimated analyte concentration of the test set is calculated, and Block 760 where an average calibration constant is calculated.

Figure 8:
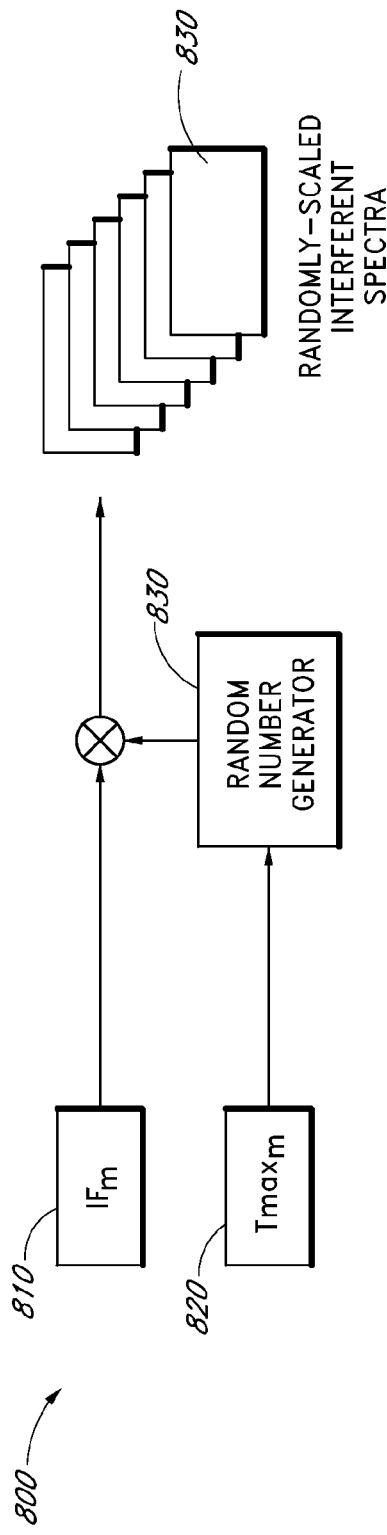
FIG. 8 is a schematic of one embodiment of a method for generating randomly-scaled interferent spectra.
Figure 9:
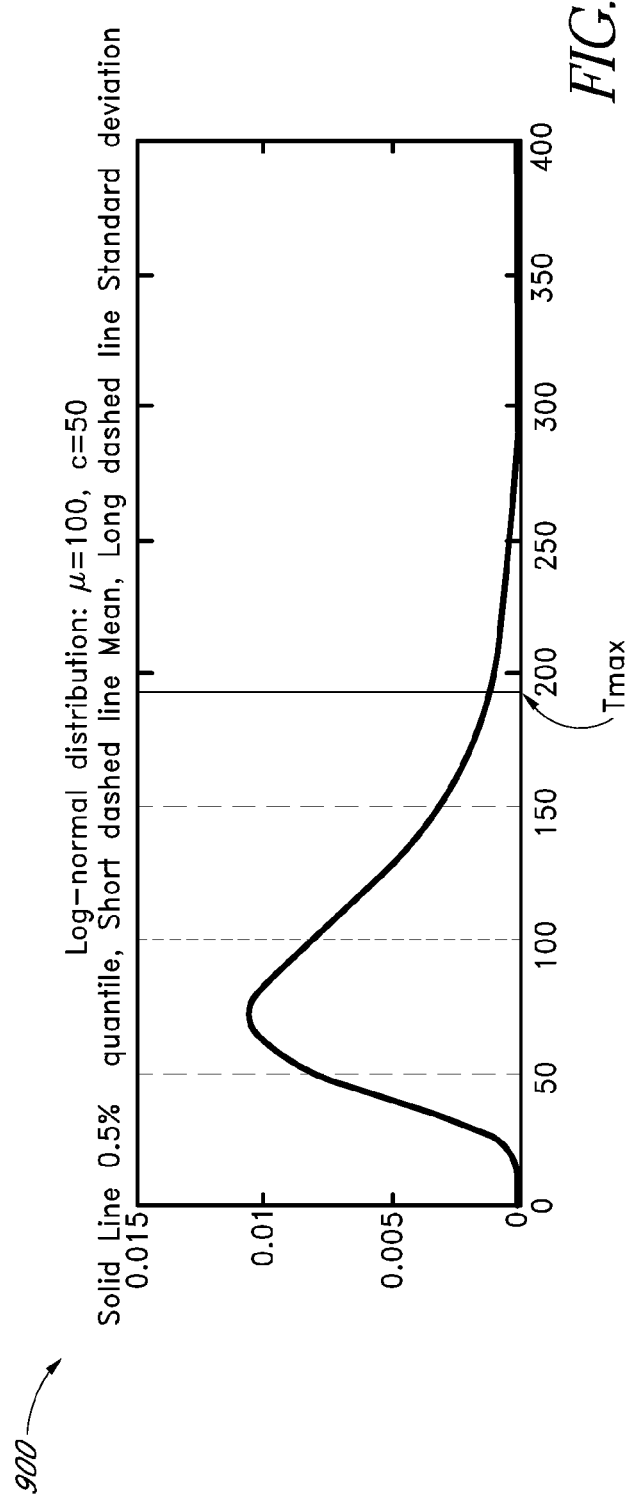
FIG. 9 is one embodiment of a distribution of interferent concentrations for use with the embodiment of FIG. 8.
Figure 10:
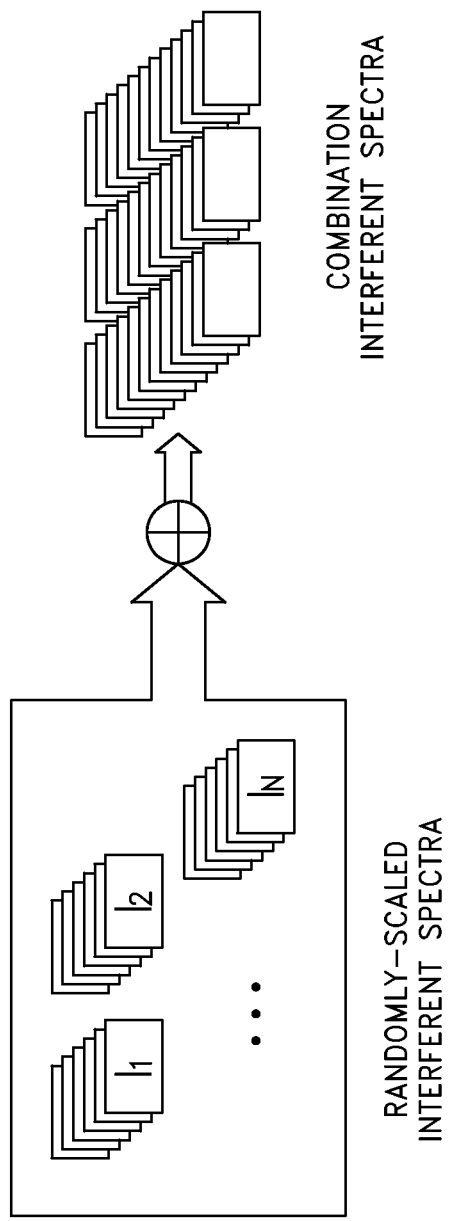
FIG. 10 is a schematic of one embodiment of a method for generating combination interferent spectra.

One embodiment of each of the methods of Blocks 710, 720, 730, 740, 750, and 760 are now described for the example of using identifying interferents in a sample for generating an average calibration constant. As indicated in Block 710, one step is to generate synthesized Sample Population spectra, by adding a random concentration of possible Library Interferents to each Sample Population spectrum. The spectra generated by the method of Block 710 are referred to herein as an Interferent-Enhanced Spectral Database, or IESD. The IESD can be formed by the steps illustrated in FIGS. 8-12, where FIG. 8 is a schematic diagram 800 illustrating the generation of Randomly-Scaled Single Interferent Spectra, or RSIS; FIG. 9 is a graph 900 of the interferent scaling; FIG. 10 is a schematic diagram illustrating the combination of RSIS into Combination Interferent Spectra, or CIS; and FIG. 11 is a schematic diagram illustrating the combination of CIS and the Sample Population spectra into an IESD.

The first step in Block 710 is shown in FIGS. 8 and 9. As shown schematically in flowchart 800 in FIG. 8, and in graph 900 in FIG. 9, a plurality of RSIS (Block 840) are formed by combinations of each previously identified Library Interferent having spectrum $IF_m$ (Block 810), multiplied by the maximum concentration $Tmax_m$ (Block 820) that is scaled by a random factor between zero and one (Block 830), as indicated by the distribution of the random number indicated in graph 900. In one embodiment, the scaling places the maximum concentration at the $95^{th}$ percentile of a log-normal distribution to produce a wide range of concentrations with the distribution having a standard deviation equal to half of its mean value. The distribution of the random numbers in graph 900 are a log-normal distribution of $\mu=100$, $\sigma=50$.

Once the individual Library Interferent spectra have been multiplied by the random concentrations to produce the RSIS, the RSIS are combined to produce a large population of interferent-only spectra, the CIS, as illustrated in FIG. 10. The individual RSIS are combined independently and in random combinations, to produce a large family of CIS, with each spectrum within the CIS consisting of a random combination of RSIS, selected from the full set of identified Library Interferents. The method illustrated in FIG. 10 produces adequate variability with respect to each interferent, independently across separate interferents.

Figure 11:
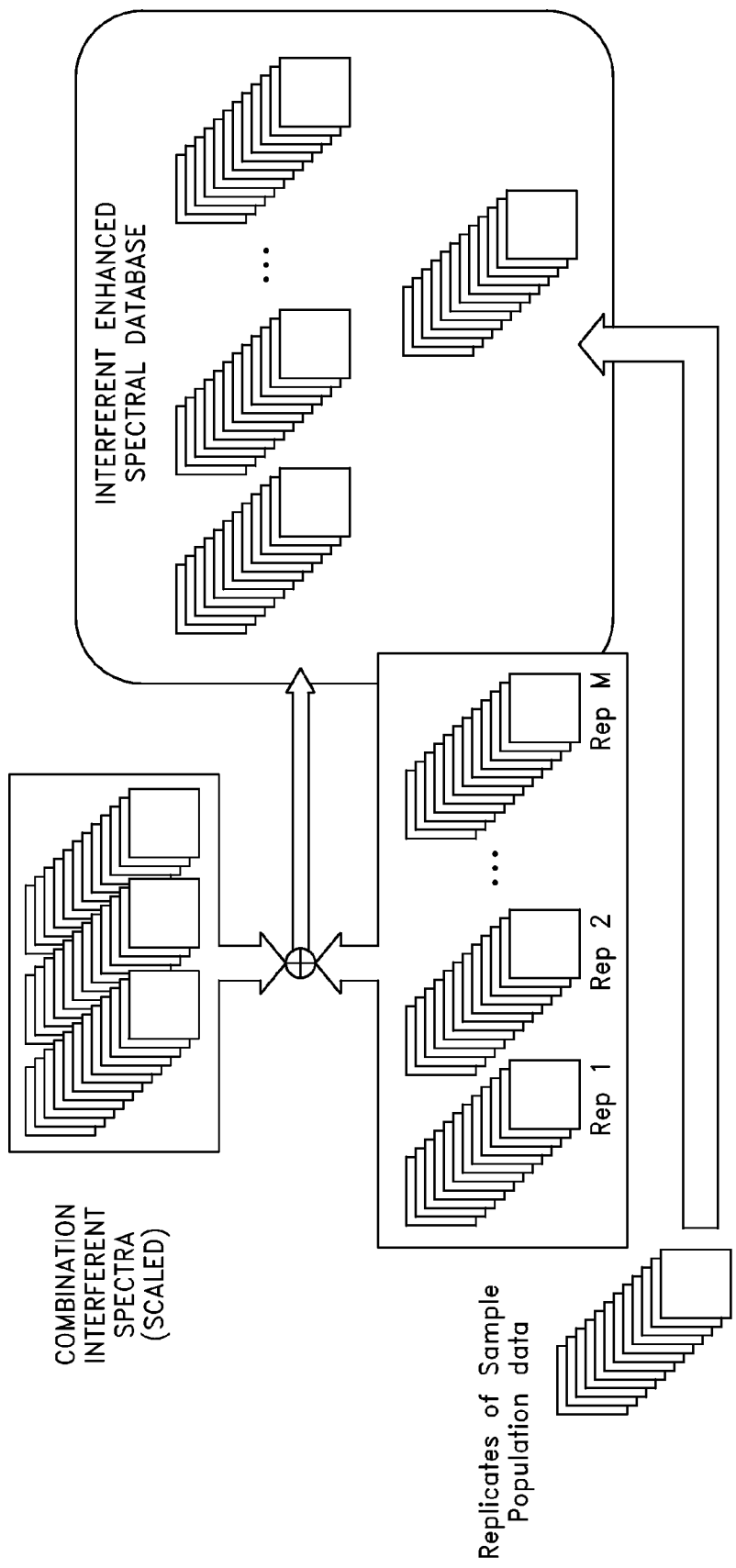
FIG. 11 is a schematic of one embodiment of a method for generating an interferent-enhanced spectral database.

The next step combines the CIS and replicates of the Sample Population spectra to form the IESD, as illustrated in FIG. 11. Since the Interferent Data and Sample Population spectra may have been obtained at different pathlengths, the CIS are first scaled (i.e., multiplied) to the same pathlength. The Sample Population database is then replicated M times, where M depends on the size of the database, as well as the number of interferents to be treated. The IESD includes M copies of each of the Sample Population spectra, where one copy is the original Sample Population Data, and the remaining M−1 copies each have an added random one of the CIS spectra. Each of the IESD spectra has an associated analyte concentration from the Sample Population spectra used to form the particular IESD spectrum.

In one embodiment, a 10-fold replication of the Sample Population database is used for 130 Sample Population spectra obtained from 58 different individuals and 18 Library Interferents. Greater spectral variety among the Library Interferent spectra requires a smaller replication factor, and a greater number of Library Interferents requires a larger replication factor.

The steps of Blocks 720, 730, 740, and 750 are executed to repeatedly combine different ones of the spectra of the IESD to statistically average out the effect of the identified Library Interferents. First, as noted in Block 720, the IESD is partitioned into two subsets: a calibration set and a test set. As described subsequently, the repeated partitioning of the IESD into different calibration and test sets improves the statistical significance of the calibration constant. In one embodiment, the calibration set is a random selection of some of the IESD spectra and the test set are the unselected IESD spectra. In a preferred embodiment, the calibration set includes approximately two-thirds of the IESD spectra.

In an alternative embodiment, the steps of Blocks 720, 730, 740, and 750 are replaced with a single calculation of an average calibration constant using all available data.

Next, as indicted in Block 730, the calibration set is used to generate a calibration constant for predicting the analyte concentration from a sample measurement. First an analyte spectrum is obtained. For the embodiment of glucose determined from absorption measurements, a glucose absorption spectrum is indicated as $a_G$. The calibration constant is then generated as follows. Using the calibration set having calibration spectra $C = \{C_1, C_2, \ldots, C_n\}$ and corresponding glucose concentration values $G = \{g_1, g_2, \ldots, g_n\}$, then glucose-free spectra $C' = \{C'_1, C'_2, \ldots, C'_n\}$ can be calculated as: $C'_j = C_j - a_G g_j$. Next, the calibration constant, $\kappa$, is calculated from $C'$ and $a_G$, according to the following 5 steps:

1) $C'$ is decomposed into $C' = A_C \Delta_C B_C$, that is, a singular value decomposition, where the A-factor is an orthonormal basis of column space, or span, of $C'$;
2) $A_C$ is truncated to avoid overfitting to a particular column rank r, based on the sizes of the diagonal entries of $\Delta$ (the singular values of $C'$). The selection of r involves a trade-off between the precision and stability of the calibration, with a larger r resulting in a more precise but less stable solution. In one embodiment, each spectrum C includes 25 wavelengths, and r ranges from 15 to 19;
3) The first r columns of $A_C$ are taken as an orthonormal basis of span $(C')$;
4) The projection from the background is found as the product $P_C = A_C \cdot A_C^T$, that is the orthogonal projection onto the span of $C$, and the complementary, or nulling projection $P_C^\perp = 1 - P_C$, which forms the projection onto the complementary subspace $C'^\perp$, is calculated; and
5) The calibration vector $\kappa$ is then found by applying the nulling projection to the absorption spectrum of the analyte of interest: $\kappa_{RAW} = P_C^\perp a_G$, and normalizing: $\kappa = \kappa_{RAW} / \langle \kappa_{RAW}, a_G \rangle$, where the angle brackets $\langle, \rangle$ denote the standard inner (or dot) product of vectors. The normalized calibration constant produces a unit response for a unit $a_G$ spectral input for one particular calibration set.

Next, the calibration constant is used to estimate the analyte concentration in the test set (Block 740). Specifically, each spectrum of the test set (each spectrum having an associated glucose concentration from the Sample Population spectra used to generate the test set) is multiplied by the calibration vector x from Block 730 to calculate an estimated glucose concentration. The error between the calculated and known glucose concentration is then calculated (Block 750). Specifically, the measure of the error can include a weighted value averaged over the entire test set according to $1/rms^2$.

Blocks 720, 730, 740, and 750 are repeated for many different random combinations of calibration sets. Preferably, Blocks 720, 730, 740, and 750 are repeated are repeated hundreds to thousands of times. Finally, an average calibration constant is calculated from the calibration and error from the many calibration and test sets (Block 760). Specifically, the average calibration is computed as weighted average calibration vector. In one embodiment the weighting is in proportion to a normalized rms, such as the $\kappa_{ave} = \kappa \cdot rms^2 / \Sigma(rms^2)$ for all tests.

With the last of Block 430 executed according to FIG. 7, the average calibration constant $\kappa_{ave}$ is applied to the obtained spectrum (Block 440).

Accordingly, one embodiment of a method of computing a calibration constant based on identified interferents can be summarized as follows:

1. Generate synthesized Sample Population spectra by adding the RSIS to raw (interferent-free) Sample Population spectra, thus forming an Interferent Enhanced Spectral Database (IESD)—each spectrum of the IESD is synthesized from one spectrum of the Sample Population, and thus each spectrum of the IESD has at least one associated known analyte concentration
2. Separate the spectra of the IESD into a calibration set of spectra and a test set of spectra
3. Generate a calibration constant for the calibration set based on the calibration set spectra and their associated known correct analyte concentrations (e.g., using the matrix manipulation outlined in five steps above)
4. Use the calibration constant generated in step 3 to calculate the error in the corresponding test set as follows (repeat for each spectrum in the test set):
   a. Multiply (the selected test set spectrum)×(average calibration constant generated in step 3) to generate an estimated glucose concentration
   b. Evaluate the difference between this estimated glucose concentration and the known, correct glucose concentration associated with the selected test spectrum to generate an error associated with the selected test spectrum
5. Average the errors calculated in step 4 to arrive at a weighted or average error for the current calibration set—test set pair
6. Repeat steps 2 through 5 n times, resulting in n calibration constants and n average errors
7. Compute a "grand average" error from the n average errors and an average calibration constant from the n calibration constants (preferably weighted averages wherein the largest average errors and calibration constants are discounted), to arrive at a calibration constant which is minimally sensitive to the effect of the identified interferents Example 1

One example of certain methods disclosed herein is illustrated with reference to the detection of glucose in blood using mid-IR absorption spectroscopy. Table 1 lists 10 Library Interferents (each having absorption features that overlap with glucose) and the corresponding maximum concentration of each Library Interferent. Table 1 also lists a Glucose Sensitivity to Interferent without and with training. The Glucose Sensitivity to Interferent is the calculated change in estimated glucose concentration for a unit change in interferent concentration. For a highly glucose selective analyte detection technique, this value is zero. The Glucose Sensitivity to Interferent without training is the Glucose Sensitivity to Interferent where the calibration has been determined using the methods above without any identified interferents. The Glucose Sensitivity to Interferent with training is the Glucose Sensitivity to Interferent where the calibration has been determined using the methods above with the appropriately identified interferents. In this case, least improvement (in terms of reduction in sensitivity to an interferent) occurs for urea, seeing a factor of 6.4 lower sensitivity, followed by three with ratios from 60 to 80 in improvement. The remaining six all have seen sensitivity factors reduced by over 100, up to over 1600. The decreased Glucose Sensitivity to Interferent with training indicates that the methods are effective at producing a calibration constant that is selective to glucose in the presence of interferents.

TABLE 1

Rejection of 10 interfering substances

| Library Interferent | Maximum Concentration | Glucose Sensitivity to Interferent w/o training | Glucose Sensitivity to Interferent w/ training |
|---|---|---|---|
| Sodium Bicarbonate | 103 | 0.330 | 0.0002 |
| Urea | 100 | −0.132 | 0.0206 |
| Magnesium Sulfate | 0.7 | 1.056 | −0.0016 |
| Naproxen | 10 | 0.600 | −0.0091 |
| Uric Acid | 12 | −0.557 | 0.0108 |
| Salicylate | 10 | 0.411 | −0.0050 |
| Glutathione | 100 | 0.041 | 0.0003 |
| Niacin | 1.8 | 1.594 | −0.0086 |
| Nicotinamide | 12.2 | 0.452 | −0.0026 |
| Chlorpropamide | 18.3 | 0.334 | 0.0012 |

Example 2

Figure 12:
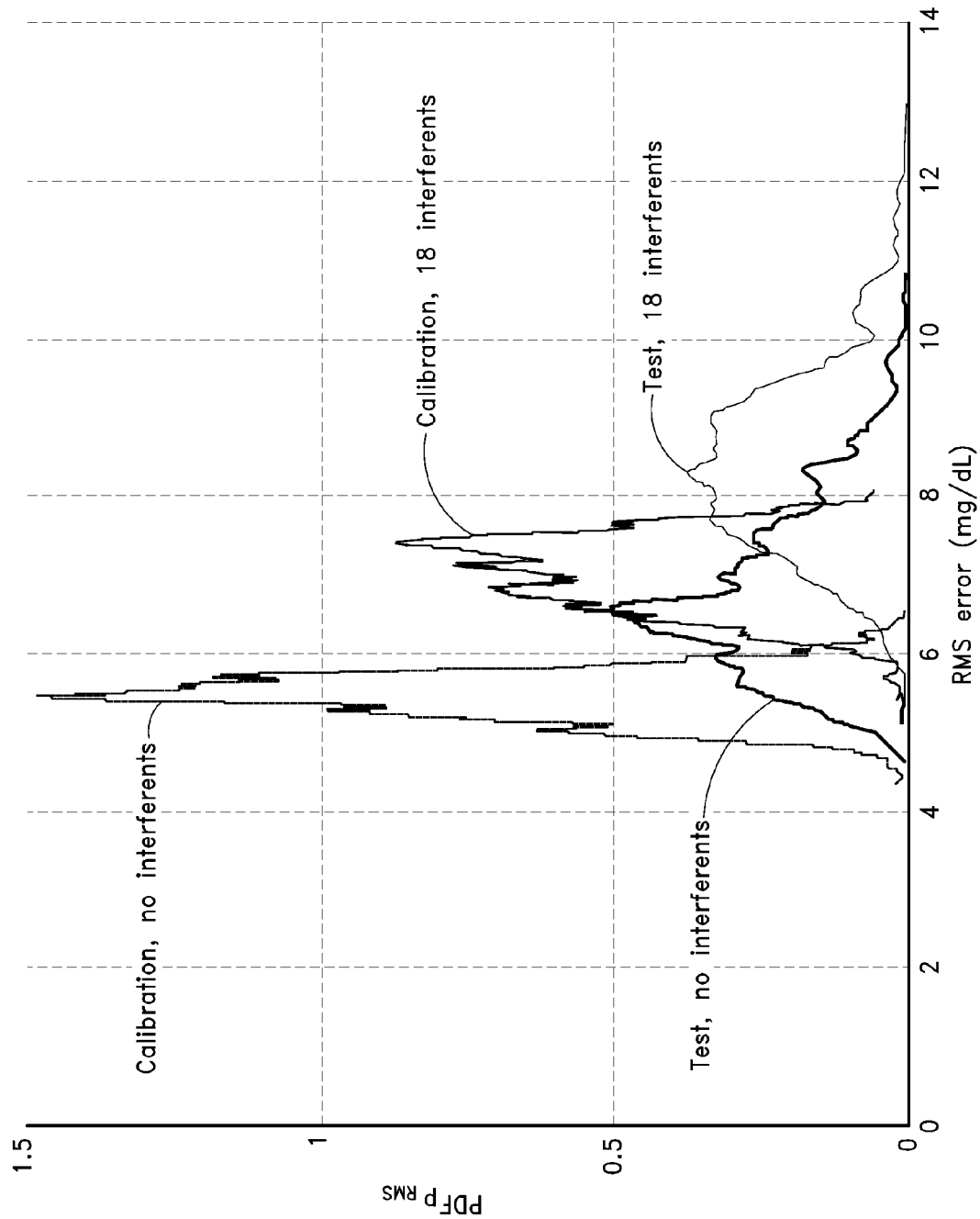
FIG. 12 is a graph illustrating the effect of interferents on the error of glucose estimation.
Figure 13A:
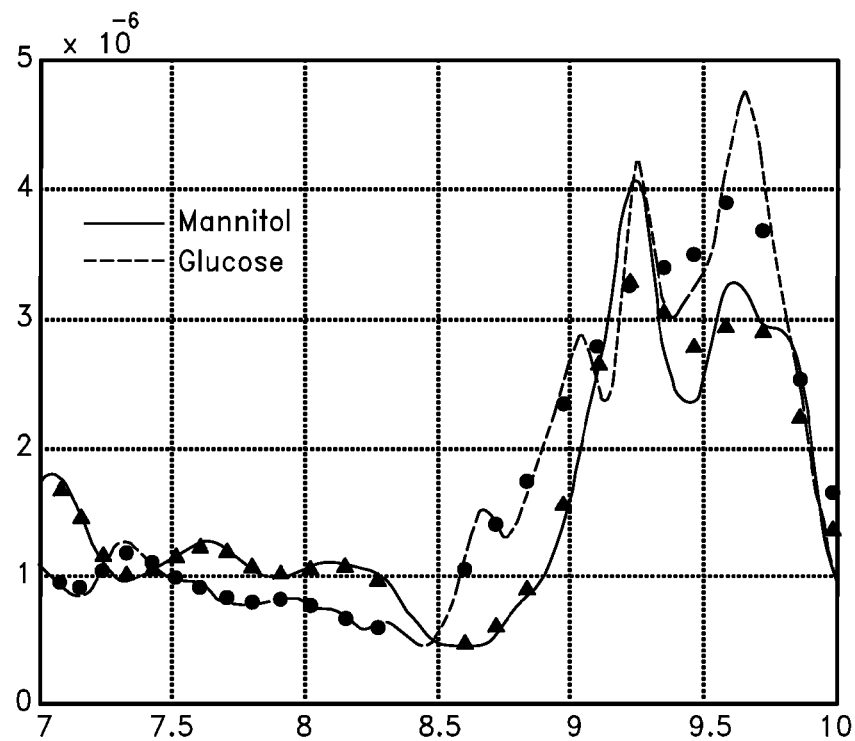
FIGS. 13A, 13B, 13C, and 13D each have a graph showing a comparison of the absorption spectrum of glucose with different interferents taken using two different techniques: a Fourier Transform Infrared (FTIR) spectrometer having an interpolated resolution of 1 $cm^{-1}$ (solid lines with triangles); and by 25 finite-bandwidth IR filters having a Gaussian profile and full-width half-maximum (FWHM) bandwidth of 28 $cm^{-1}$ corresponding to a bandwidth that varies from 140 nm at 7.08 µm, up to 279 nm at 10 µm (dashed lines with circles). The Figures show a comparison of glucose with mannitol (FIG. 13A), dextran (FIG. 13B), n-acetyl L cysteine (FIG. 13C), and procainamide (FIG. 13D), at a concentration level of 1 mg/dL and path length of 1 µm.
Figure 13B:
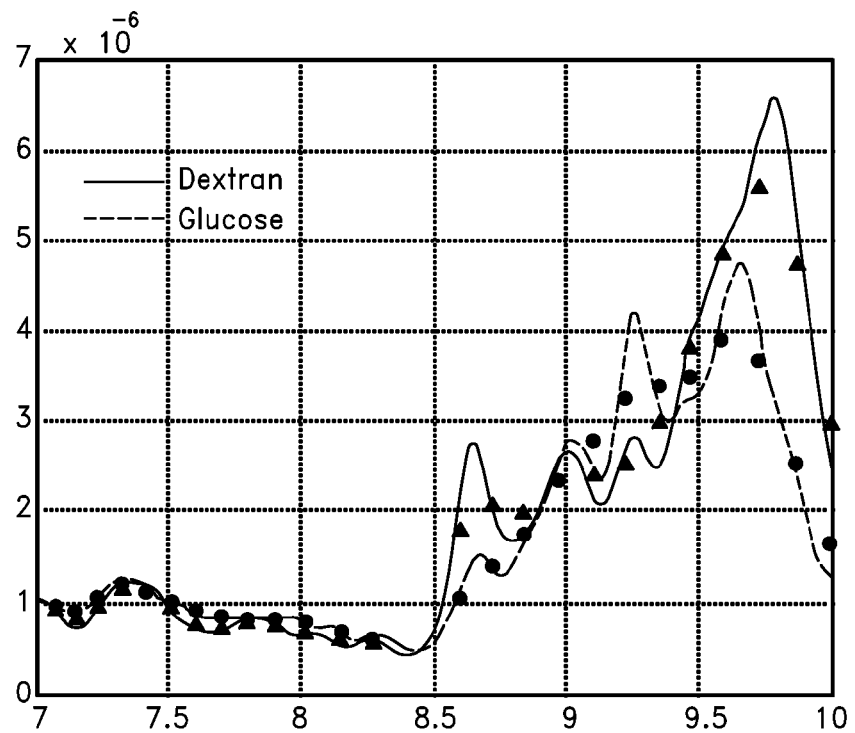
Figure 13C:
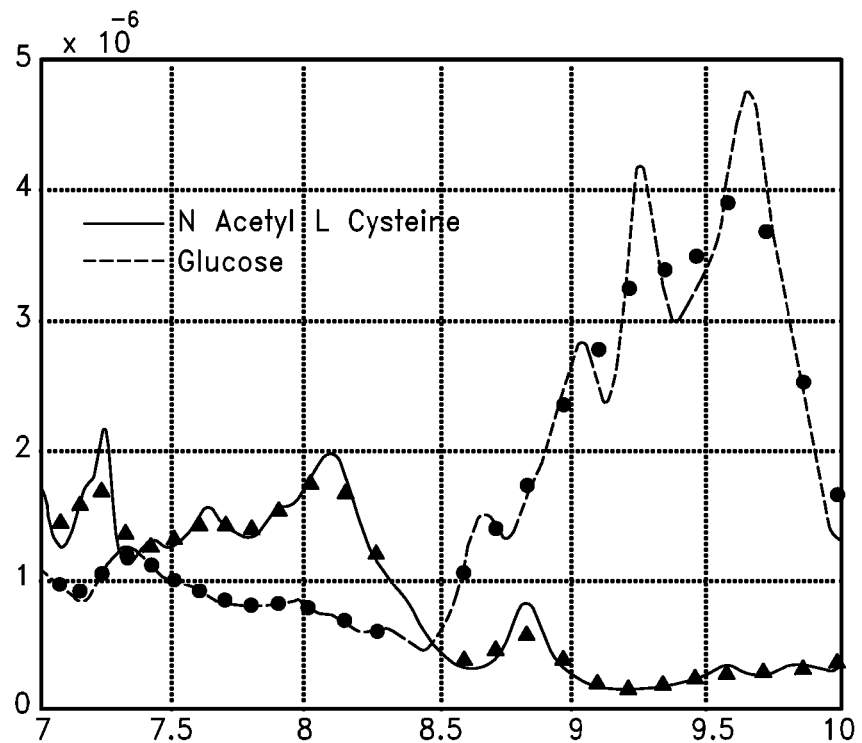
Figure 13D:
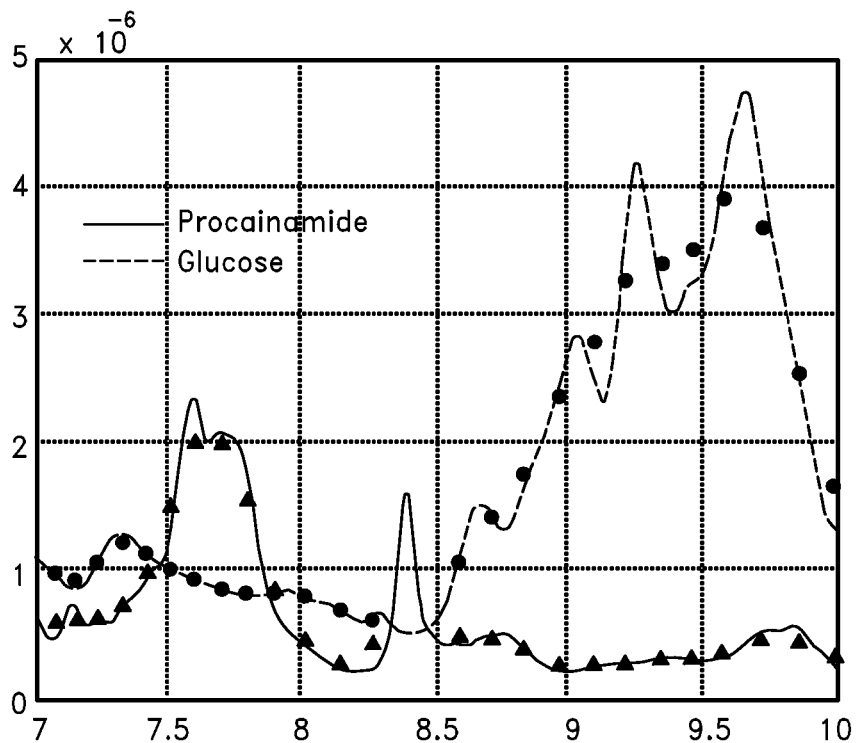

Another example illustrates the effect of the methods for 18 interferents. Table 2 lists of 18 interferents and maximum concentrations that were modeled for this example, and the glucose sensitivity to the interferent without and with training. The table summarizes the results of a series of 1000 calibration and test simulations that were performed both in the absence of the interferents, and with all interferents present. FIG. 12 shows the distribution of the R.M.S. error in the glucose concentration estimation for 1000 trials. While a number of substances show significantly less sensitivity (sodium bicarbonate, magnesium sulfate, tolbutamide), others show increased sensitivity (ethanol, acetoacetate), as listed in Table 2. The curves in FIG. 12 are for calibration set and the test set both without any interferents and with all 18 interferents. The interferent produces a degradation of performance, as can be seen by comparing the calibration or test curves of FIG. 12. Thus, for example, the peaks appear to be shifted by about 2 mg/dL, and the width of the distributions is increased slightly. The reduction in height of the peaks is due to the spreading of the distributions, resulting in a modest degradation in performance.

TABLE 2

List of 18 Interfering Substances with maximum concentrations and Sensitivity with respect to interferents, with/without training

| | Library Interferent | Conc. (mg/dL) | Glucose Sensitivity to Interferent w/o training | Glucose Sensitivity to Interferent w/ training |
|---|---|---|---|---|
| 1 | Urea | 300 | −0.167 | −0.100 |
| 2 | Ethanol | 400.15 | −0.007 | −0.044 |
| 3 | Sodium Bicarbonate | 489 | 0.157 | −0.093 |
| 4 | Acetoacetate Li | 96 | 0.387 | 0.601 |
| 5 | Hydroxybutyric Acid | 465 | −0.252 | −0.101 |
| 6 | Magnesium Sulfate | 29.1 | 2.479 | 0.023 |
| 7 | Naproxen | 49.91 | 0.442 | 0.564 |
| 8 | Salicylate | 59.94 | 0.252 | 0.283 |
| 9 | Ticarcillin Disodium | 102 | −0.038 | −0.086 |
| 10 | Cefazolin | 119.99 | −0.087 | −0.006 |
| 11 | Chlorpropamide | 27.7 | 0.387 | 0.231 |
| 12 | Nicotinamide | 36.6 | 0.265 | 0.366 |
| 13 | Uric Acid | 36 | −0.641 | −0.712 |
| 14 | Ibuprofen | 49.96 | −0.172 | −0.125 |
| 15 | Tolbutamide | 63.99 | 0.132 | 0.004 |
| 16 | Tolazamide | 9.9 | 0.196 | 0.091 |
| 17 | Bilirubin | 3 | −0.391 | −0.266 |
| 18 | Acetaminophen | 25.07 | 0.169 | 0.126 |

Example 3

In a third example, certain methods disclosed herein were tested for measuring glucose in blood using mid-IR absorption spectroscopy in the presence of four interferents not normally found in blood (Type-B interferents) and that may be common for patients in hospital intensive care units (ICUs). The four Type-B interferents are mannitol, dextran, n-acetyl L cysteine, and procainamide.

Of the four Type-B interferents, mannitol and dextran have the potential to interfere substantially with the estimation of glucose: both are spectrally similar to glucose (see FIG. 1), and the dosages employed in ICUs are very large in comparison to typical glucose levels. Mannitol, for example, may be present in the blood at concentrations of 2500 mg/dL, and dextran may be present at concentrations in excess of 5000 mg/dL. For comparison, typical plasma glucose levels are on the order of 100-200 mg/dL. The other Type-B interferents, n-acetyl L cysteine and procainamide, have spectra that are quite unlike the glucose spectrum.

FIGS. 13A, 13B, 13C, and 13D each have a graph showing a comparison of the absorption spectrum of glucose with different interferents taken using two different techniques: a Fourier Transform Infrared (FTIR) spectrometer having an interpolated resolution of 1 cm$^{-1}$ (solid lines with triangles); and by 25 finite-bandwidth IR filters having a Gaussian profile and full-width half-maximum (FWHM) bandwidth of 28 cm$^{-1}$ corresponding to a bandwidth that varies from 140 nm at 7.08 μm, up to 279 nm at 10 μm (dashed lines with circles). Specifically, the figures show a comparison of glucose with mannitol (FIG. 13A), with dextran (FIG. 13B), with n-acetyl L cysteine (FIG. 13C), and with procainamide (FIG. 13D), at a concentration level of 1 mg/dL and path length of 1 μm. The horizontal axis in FIGS. 13A-13D has units of wavelength in microns (μm), ranging from 7 μm to 10 μm, and the vertical axis has arbitrary units.

The central wavelength of the data obtained using filter is indicated in FIGS. 13A, 13B, 13C, and 13D by the circles along each dashed curve, and corresponds to the following wavelengths, in microns: 7.082, 7.158, 7.241, 7.331, 7.424, 7.513, 7.605, 7.704, 7.800, 7.905, 8.019, 8.150, 8.271, 8.598, 8.718, 8.834, 8.969, 9.099, 9.217, 9.346, 9.461, 9.579, 9.718, 9.862, and 9.990. The effect of the bandwidth of the filters on the spectral features can be seen in FIGS. 13A-13D as the decrease in the sharpness of spectral features on the solid curves and the relative absence of sharp features on the dashed curves.

Figure 14:
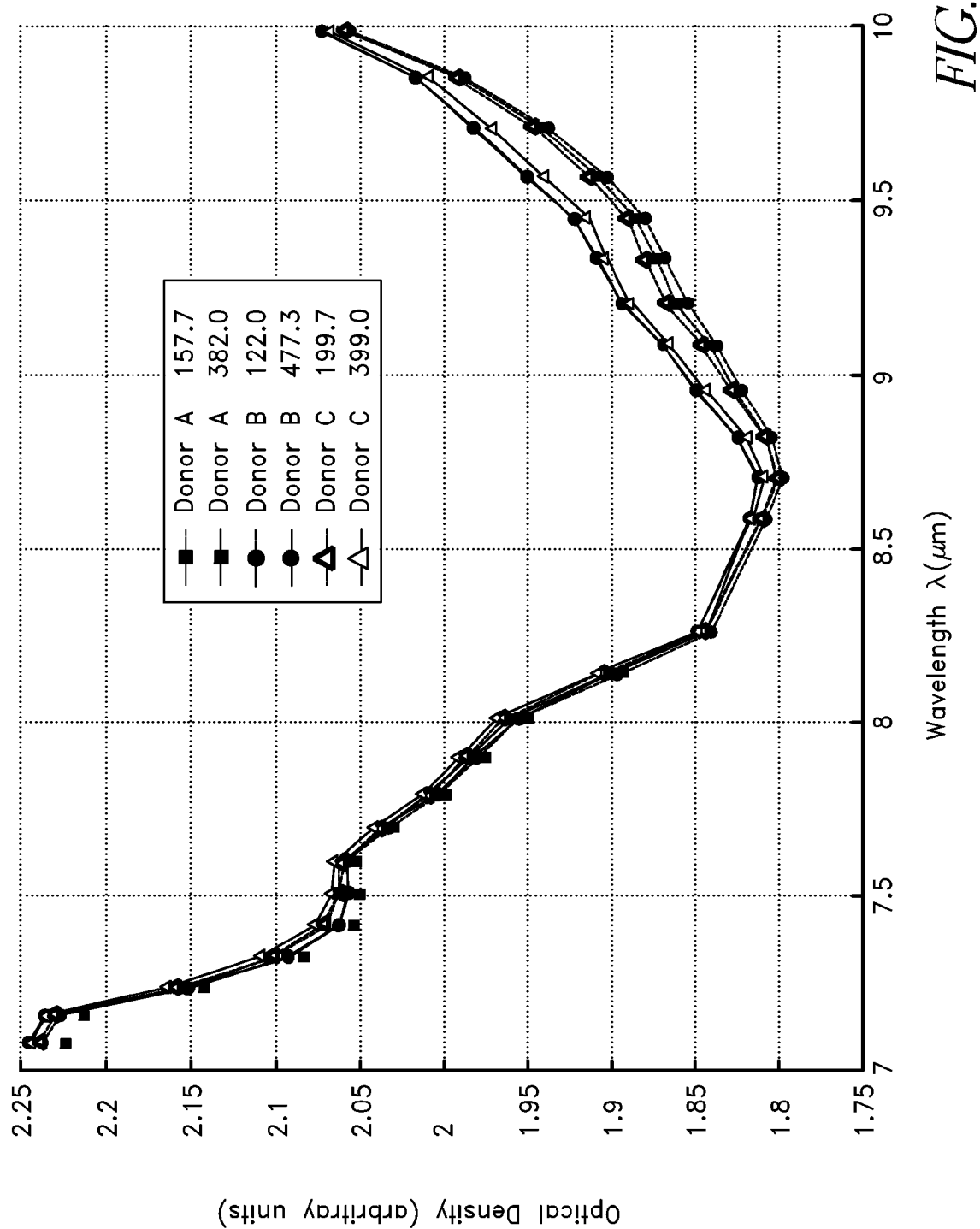
FIG. 14 shows a graph of the blood plasma spectra for 6 blood sample taken from three donors in arbitrary units for a wavelength range from 7 µm to 10 µm, where the symbols on the curves indicate the central wavelengths of the 25 filters.
Figure 15A:
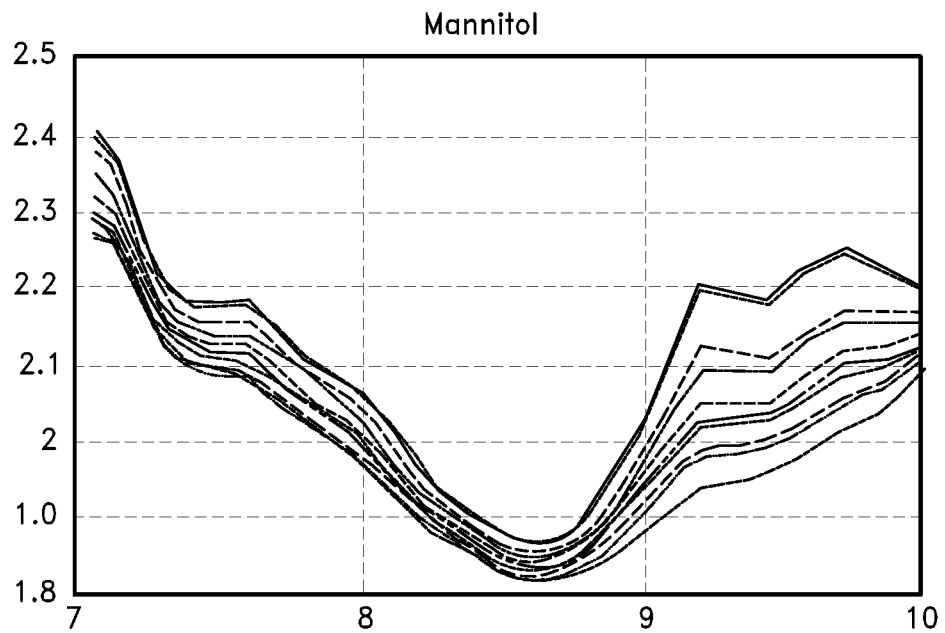
FIGS. 15A, 15B, 15C, and 15D contain spectra of the Sample Population of 6 samples having random amounts of mannitol (FIG. 15A), dextran (FIG. 15B), n-acetyl L cysteine (FIG. 15C), and procainamide (FIG. 15D), at a concentration levels of 1 mg/dL and path lengths of 1 µm.
Figure 15B:
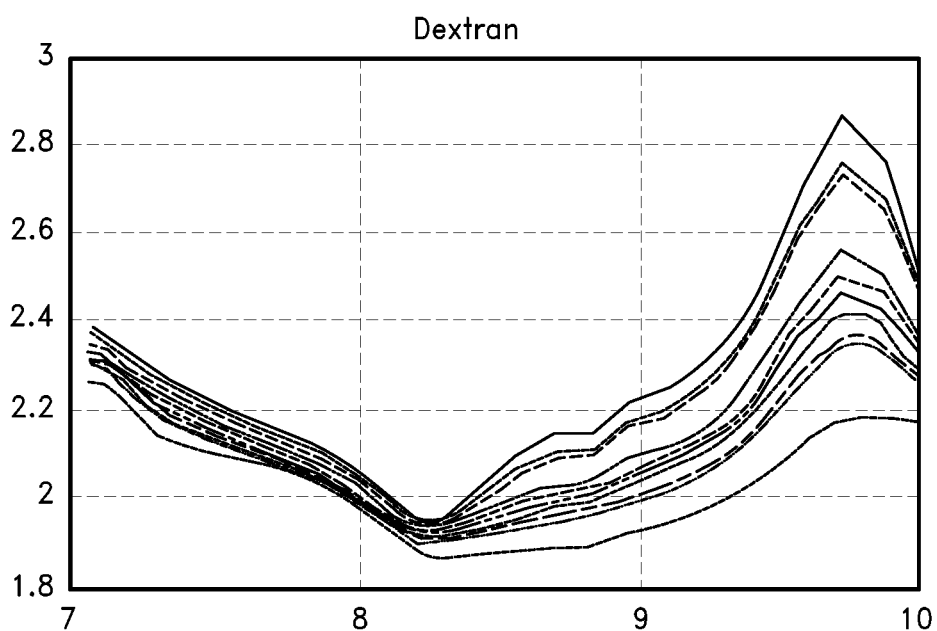
Figure 15C:
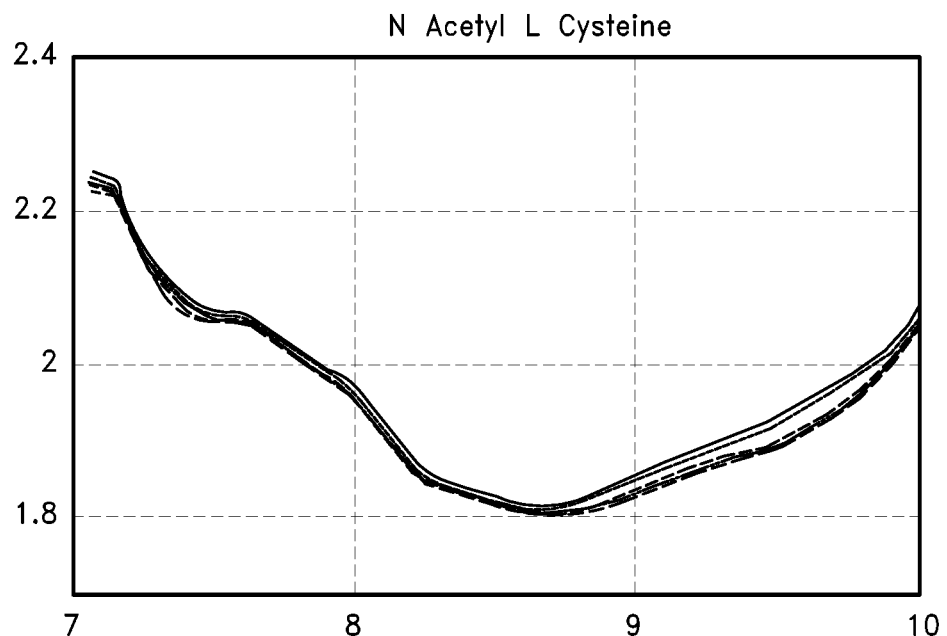
Figure 15D:
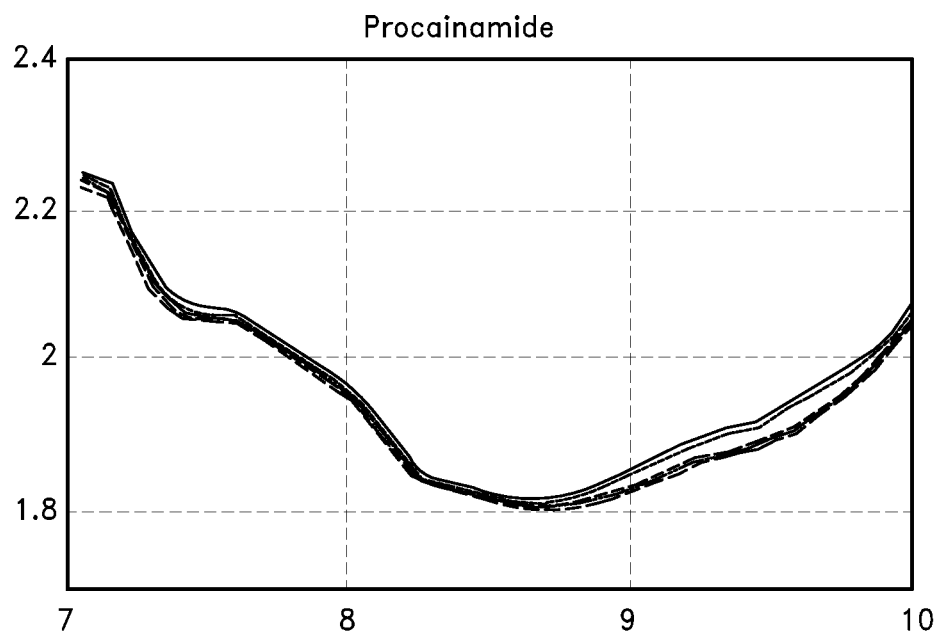
Figure 16A:
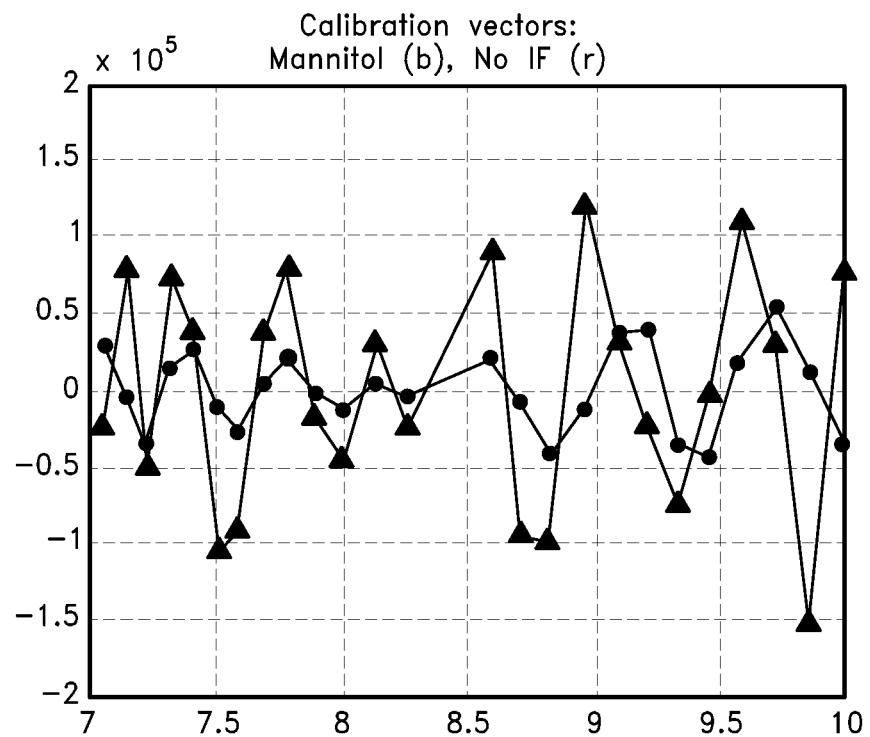
FIGS. 16A-16D are graphs comparing calibration vectors obtained by training in the presence of an interferent, to the calibration vector obtained by training on clean plasma spectra for mannitol (FIG. 16A), dextran (FIG. 16B), n-acetyl L cysteine (FIG. 16C), and procainamide (FIG. 16D) for water-free spectra.
Figure 16B:
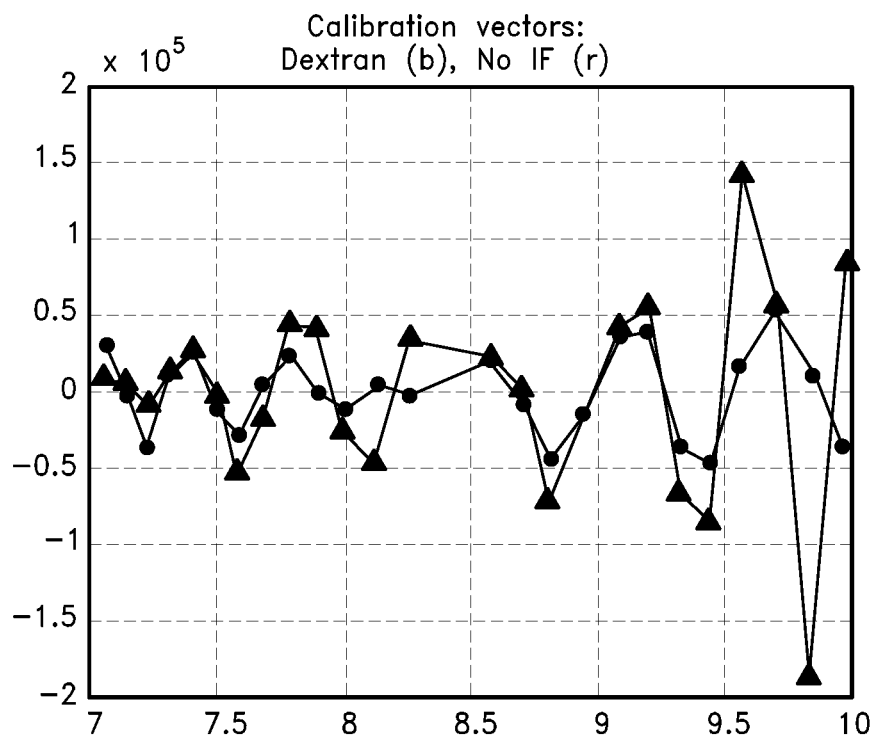
Figure 16C:
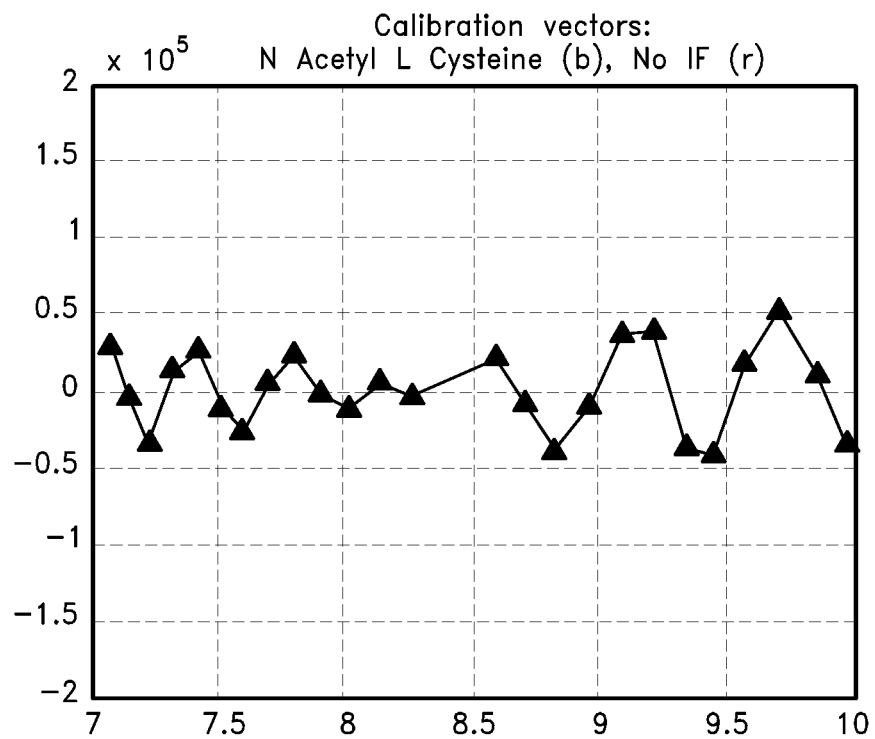
Figure 16D:
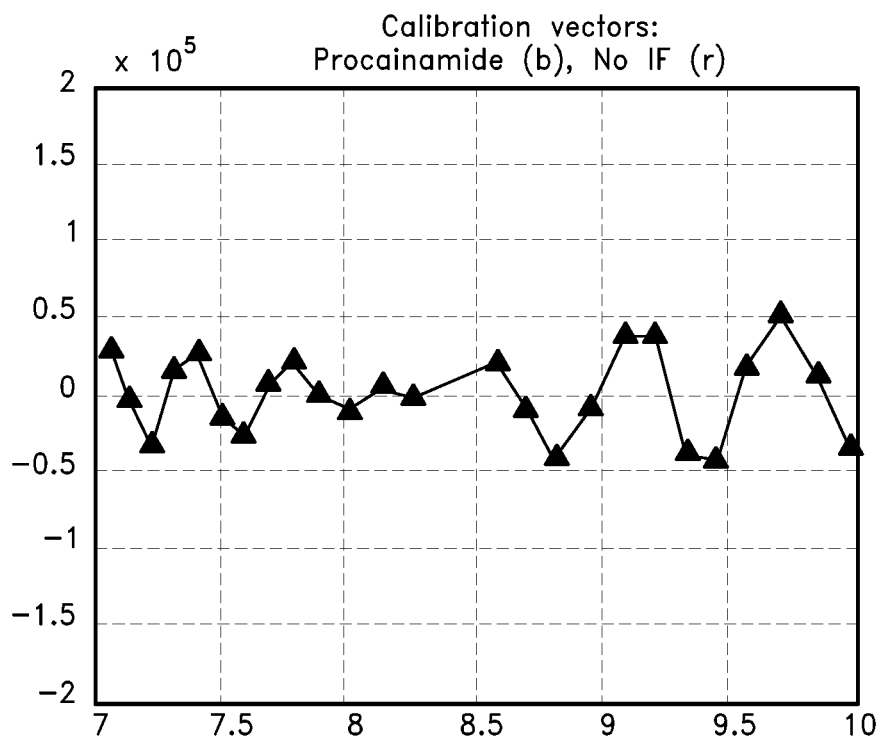

FIG. 14 shows a graph of the blood plasma spectra for 6 blood samples taken from three donors in arbitrary units for a wavelength range from 7 μm to 10 μm, where the symbols on the curves indicate the central wavelengths of the 25 filters. The 6 blood samples do not contain any mannitol, dextran, n-acetyl L cysteine, and procainamide—the Type-B interferents of this Example, and are thus a Sample Population. Three donors (indicated as donor A, B, and C) provided blood at different times, resulting in different blood glucose levels, shown in the graph legend in mg/dL as measured using a YSI Biochemistry Analyzer (YSI Incorporated, Yellow Springs, Ohio). The path length of these samples, estimated at 36.3 μm by analysis of the spectrum of a reference scan of saline in the same cell immediately prior to each sample spectrum, was used to normalize these measurements. This quantity was taken into account in the computation of the calibration vectors provided, and the application of these vectors to spectra obtained from other equipment would require a similar pathlength estimation and normalization process to obtain valid results.

Next, random amounts of each Type-B interferent of this Example are added to the spectra to produce mixtures that, for example could make up an Interferent Enhanced Spectral. Each of the Sample Population spectra was combined with a random amount of a single interferent added, as indicated in Table 3, which lists an index number N, the Donor, the glucose concentration (GLU), interferent concentration (conc (IF)), and the interferent for each of 54 spectra. The conditions of Table 3 were used to form combined spectra including each of the 6 plasma spectra was combined with 2 levels of each of the 4 interferents.

TABLE 3

Interferent Enhanced Spectral Database for Example 3.

| N | Donor | GLU | conc(IF) | IF |
|---|---|---|---|---|
| 1 | A | 157.7 | | N/A |
| 2 | A | 382 | | N/A |
| 3 | B | 122 | | N/A |
| 4 | B | 477.3 | | N/A |
| 5 | C | 199.7 | | N/A |
| 6 | C | 399 | | N/A |
| 7 | A | 157.7 | 1001.2 | Mannitol |
| 8 | A | 382 | 2716.5 | Mannitol |
| 9 | A | 157.7 | 1107.7 | Mannitol |
| 10 | A | 382 | 1394.2 | Mannitol |
| 11 | B | 122 | 2280.6 | Mannitol |
| 12 | B | 477.3 | 1669.3 | Mannitol |
| 13 | B | 122 | 1710.2 | Mannitol |
| 14 | B | 477.3 | 1113.0 | Mannitol |
| 15 | C | 199.7 | 1316.4 | Mannitol |
| 16 | C | 399 | 399.1 | Mannitol |
| 17 | C | 199.7 | 969.8 | Mannitol |
| 18 | C | 399 | 2607.7 | Mannitol |
| 19 | A | 157.7 | 8.8 | N Acetyl L Cysteine |
| 20 | A | 382 | 2.3 | N Acetyl L Cysteine |
| 21 | A | 157.7 | 3.7 | N Acetyl L Cysteine |
| 22 | A | 382 | 8.0 | N Acetyl L Cysteine |
| 23 | B | 122 | 3.0 | N Acetyl L Cysteine |
| 24 | B | 477.3 | 4.3 | N Acetyl L Cysteine |
| 25 | B | 122 | 8.4 | N Acetyl L Cysteine |
| 26 | B | 477.3 | 5.8 | N Acetyl L Cysteine |
| 27 | C | 199.7 | 7.1 | N Acetyl L Cysteine |
| 28 | C | 399 | 8.5 | N Acetyl L Cysteine |
| 29 | C | 199.7 | 4.4 | N Acetyl L Cysteine |
| 30 | C | 399 | 4.3 | N Acetyl L Cysteine |
| 31 | A | 157.7 | 4089.2 | Dextran |
| 32 | A | 382 | 1023.7 | Dextran |
| 33 | A | 157.7 | 1171.8 | Dextran |
| 34 | A | 382 | 4436.9 | Dextran |
| 35 | B | 122 | 2050.6 | Dextran |
| 36 | B | 477.3 | 2093.3 | Dextran |
| 37 | B | 122 | 2183.3 | Dextran |
| 38 | B | 477.3 | 3750.4 | Dextran |
| 39 | C | 199.7 | 2598.1 | Dextran |
| 40 | C | 399 | 2226.3 | Dextran |
| 41 | C | 199.7 | 2793.0 | Dextran |
| 42 | C | 399 | 2941.8 | Dextran |
| 43 | A | 157.7 | 22.5 | Procainamide |
| 44 | A | 382 | 35.3 | Procainamide |
| 45 | A | 157.7 | 5.5 | Procainamide |
| 46 | A | 382 | 7.7 | Procainamide |
| 47 | B | 122 | 18.5 | Procainamide |
| 48 | B | 477.3 | 5.6 | Procainamide |
| 49 | B | 122 | 31.8 | Procainamide |
| 50 | B | 477.3 | 8.2 | Procainamide |
| 51 | C | 199.7 | 22.0 | Procainamide |
| 52 | C | 399 | 9.3 | Procainamide |
| 53 | C | 199.7 | 19.7 | Procainamide |
| 54 | C | 399 | 12.5 | Procainamide |

FIGS. 15A, 15B, 15C, and 15D contain spectra formed from the conditions of Table 3. Specifically, the figures show spectra of the Sample Population of 6 samples having random amounts of mannitol (FIG. 15A), dextran (FIG. 15B), n-acetyl L cysteine (FIG. 15C), and procainamide (FIG. 15D), at a concentration levels of 1 mg/dL and path lengths of 1 μm.

Next, calibration vectors were generated using the spectra of FIGS. 15A-15D, in effect reproducing the steps of Block 420. The next step of this Example is the spectral subtraction of water that is present in the sample to produce water-free spectra. As discussed above, certain methods disclosed herein provide for the estimation of an analyte concentration in the presence of interferents that are present in both a sample population and the measurement sample (Type-A interferents), and it is not necessary to remove the spectra for interferents present in Sample Population and sample being measured. The step of removing water from the spectrum is thus an alternative embodiment of the disclosed methods.

The calibration vectors are shown in FIGS. 16A-16D for mannitol (FIG. 16A), dextran (FIG. 16B), n-acetyl L cysteine (FIG. 16C), and procainamide (FIG. 16D) for water-free spectra. Specifically each one of FIGS. 16A-16D compares calibration vectors obtained by training in the presence of an interferent, to the calibration vector obtained by training on clean plasma spectra alone. The calibration vector is used by computing its dot-product with the vector representing (pathlength-normalized) spectral absorption values for the filters used in processing the reference spectra. Large values (whether positive or negative) typically represent wavelengths for which the corresponding spectral absorbance is sensitive to the presence of glucose, while small values generally represent wavelengths for which the spectral absorbance is insensitive to the presence of glucose. In the presence of an interfering substance, this correspondence is somewhat less transparent, being modified by the tendency of interfering substances to mask the presence of glucose.

The similarity of the calibration vectors obtained for minimizing the effects of the two interferents n-acetyl L cysteine and procainamide, to that obtained for pure plasma, is a reflection of the fact that these two interferents are spectrally quite distinct from the glucose spectrum; the large differences seen between the calibration vectors for minimizing the effects of dextran and mannitol, and the calibration obtained for pure plasma, are conversely representative of the large degree of similarity between the spectra of these substances and that of glucose. For those cases in which the interfering spectrum is similar to the glucose spectrum (that is, mannitol and dextran), the greatest change in the calibration vector. For those cases in which the interfering spectrum is different from the glucose spectrum (that is, n-acetyl L cysteine and procainamide), it is difficult to detect the difference between the calibration vectors obtained with and without the interferent.

It will be understood that the steps of methods discussed are performed in one embodiment by an appropriate processor (or processors) of a processing (i.e., computer) system executing instructions (code segments) stored in appropriate storage. It will also be understood that the disclosed methods and apparatus are not limited to any particular implementation or programming technique and that the methods and apparatus may be implemented using any appropriate techniques for implementing the functionality described herein. The methods and apparatus are not limited to any particular programming language or operating system. In addition, the various components of the apparatus may be included in a single housing or in multiple housings that communication by wire or wireless communication.

Further, the interferent, analyte, or population data used in the method may be updated, changed, added, removed, or otherwise modified as needed. Thus, for example, spectral information and/or concentrations of interferents that are accessible to the methods may be updated or changed by updating or changing a database of a program implementing the method. The updating may occur by providing new computer readable media or over a computer network. Other changes that may be made to the methods or apparatus include, but are not limited to, the adding of additional analytes or the changing of population spectral information.

One embodiment of each of the methods described herein may include a computer program accessible to and/or executable by a processing system, e.g., a one or more processors and memories that are part of an embedded system. Thus, as will be appreciated by those skilled in the art, embodiments of the disclosed inventions may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, various ones of the disclosed inventions may take the form of a method, an entirely hardware embodiment, an entirely software embodiment or an embodiment combining software and hardware aspects. Furthermore, any one or more of the disclosed methods (including but not limited to the disclosed methods of measurement analysis, interferent determination, and/or calibration constant generation) may be stored as one or more computer readable code segments or data compilations on a carrier medium. Any suitable computer readable carrier medium may be used including a magnetic storage device such as a diskette or a hard disk; a memory cartridge, module, card or chip (either alone or installed within a larger device); or an optical storage device such as a CD or DVD.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments, various features of the inventions are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

Further information on analyte detection systems, sample elements, algorithms and methods for computing analyte concentrations, and other related apparatus and methods can be found in U.S. Patent Application Publication No. 2003/0090649, published May 15, 2003, titled REAGENT-LESS WHOLE BLOOD GLUCOSE METER; U.S. Patent Application Publication No. 2003/0178569, published Sep. 25, 2003, titled PATHLENGTH-INDEPENDENT METHODS FOR OPTICALLY DETERMINING MATERIAL COMPOSITION; U.S. Patent Application Publication No. 2004/0019431, published Jan. 29, 2004, titled METHOD OF DETERMINING AN ANALYTE CONCENTRATION IN A SAMPLE FROM AN ABSORPTION SPECTRUM; U.S. Patent Application Publication No. 2005/0036147, published Feb. 17, 2005, titled METHOD OF DETERMINING ANALYTE CONCENTRATION IN A SAMPLE USING INFRARED TRANSMISSION DATA; and U.S. Patent Application Publication No. 2005/0038357, published on Feb. 17, 2005, titled SAMPLE ELEMENT WITH BARRIER MATERIAL. The entire contents of each of the above-mentioned publications are hereby incorporated by reference herein and are made a part of this specification.

A number of applications, publications and external documents are incorporated by reference herein. Any conflict or contradiction between a statement in the bodily text of this specification and a statement in any of the incorporated documents is to be resolved in favor of the statement in the bodily text.

What is claimed is:

1. A method for estimating the concentration of an analyte in a fluid sample, the method comprising:
   drawing a fluid sample into an automated monitoring system connected to a patient;
   using the system to separate a first interferent from the fluid sample, the remainder comprising a fluid analysis sample;
   performing a measurement of the fluid analysis sample;
   identifying, based on the measurement of the fluid analysis sample, a second interferent to the estimation of the analyte, the second interferent located in the fluid analysis sample;
   calculating a calibration constant which reduces error attributable to the second interferent, the calibration constant based at least partly on the measurement of the fluid analysis sample identifying the second interferent;
   applying the calibration constant to the measurement; and
   estimating, based on the calibrated measurement, the analyte concentration in the fluid analysis sample.

2. The method of claim 1, wherein the calculating a calibration constant is done without information on the concentration in the analysis sample of the second interferent.

3. The method of claim 1, wherein the fluid sample is a sample from a person, wherein the identifying includes comparing the measurement with population measurements modified to include concentrations of the second interferent, and where the population does not necessarily include the person.

4. The method of claim 1, where the fluid sample includes at least one component of blood, and the analyte is glucose.

5. The method of claim 1, where the fluid sample comprises blood, the first interferent comprises red blood cells, and the separating comprises filtering or centrifuging the sample.

6. The method of claim 1, where the fluid sample comprises at least one component of blood, and the first interferent comprises an exogenous interferent.

7. The method of claim 1, where the measurement is a spectrum.

8. The method of claim 7, wherein the calibration constant is a vector that is not required to be perpendicular to a spectrum of the second interferent.

9. The method of claim 1, where the calculating minimizes errors in the calibration constant due to the presence of the second interferent in the analysis sample.

10. A system for estimating the concentration of an analyte in a sample, the system comprising:
   a fluid network configured to connect to a patient and draw fluid samples therefrom;
   a separating apparatus configured to receive the fluid sample and separate a first interferent from the sample, the remainder comprising an analysis sample;
   an apparatus configured to perform a measurement of the analysis sample;
   an identifying apparatus configured to identify, based on the measurement of the analysis sample, a second interferent to the estimation of the analyte in the sample, the second interferent located in the analysis sample;
   a calibration processor configured to calculate a calibration constant which reduces error attributable to the second interferent, the calibration constant based at least partly on the measurement of the fluid analysis sample identifying the second interferent;
   the calibration processor further configured to apply the calibration constant to the measurement; and
   an estimating apparatus configured to estimate, based on the calibrated measurement, the analyte concentration in the sample.

11. The system of claim 10, wherein the separating apparatuses comprises a filter or a centrifuge.

12. The system of claim 10, wherein the first interferent comprises an endogenous interferent and the second interferent comprises an exogenous interferent.

13. The system of claim 10, wherein the sample comprises blood, the first interferent comprises blood cells, and the second interferent comprises a chemical species.

14. The system of claim 10, wherein the apparatus configured to perform a measurement comprises a spectroscope.

15. The system of claim 14, wherein the calibration processor is configured to calculate the calibration constant such that the calibration constant is a vector that is not required to be perpendicular to a spectrum of the second interferent.

16. An analyte detection system comprising:
   a fluid network configured to be connected to a patient and receive periodic sample withdrawals therefrom;
   a separator for separating a first interferent from a sample to provide an analysis sample;
   a sensor configured to provide information relating to a measurement of an analyte in the analysis sample;
   a processor; and
   a computer storage medium having stored program instructions executable by the processor such that the system is configured to:
   identify, based on the measurement of the analysis sample after the first interferent has been separated, a second interferent to the estimation of the analyte in the sample;
   calculate, based on the identified second interferent, a calibration which reduces error attributable to the second interferent, the calibration comprising determining a calibration constant;
   apply the calibration to the measurement; and
   estimate, based on the calibrated measurement, the analyte concentration in the sample.

17. The analyte detection system of claim 16, wherein the separator comprises a filter or a centrifuge.

18. The analyte detection system of claim 16, wherein the sensor comprises a spectroscope.

19. The analyte detection system of claim 16, wherein the sample comprises blood, the first interferent comprises red blood cells, and the second interferent comprises at least one of an endogenous interferent or an exogenous interferent.

20. The analyte detection system of claim 16, wherein the system is configured to calculate the calibration without information on the concentration in the analysis sample of the second interferent.

21. A method for determining a concentration of an analyte in a portion of a fluid sample from a patient, the method comprising:
   providing a fluid handling system in fluid communication with a fluid source in a patient, the fluid handling system configured to draw a plurality of fluid samples while in continuous fluid communication with the fluid source in the patient, said plurality of fluid samples comprising at least a first fluid sample and a second fluid sample, the second fluid sample drawn after the first fluid sample;
   drawing, via the fluid handling system, the first fluid sample from the patient, the first fluid sample comprising blood or a component of blood;
   transporting, via the fluid handling system, a portion of the first fluid sample to an analysis system;
   removing a first interference from the first fluid sample;
   identifying based on a measurement of the first fluid sample, a second interference to a determination of a concentration of an analyte in the first fluid sample, the second interference located in the first fluid sample;
   correcting for the second interference by using the measurement of the first fluid sample to calculate a calibration constant;
   applying the calibration constant to the measurement;
   wherein the fluid handling system is configured to remain in fluid communication with the fluid source in the patient during said drawing, said transporting, and said correcting, and
   wherein said correcting occurs before drawing the second fluid sample from the fluid source in the patient.

22. The method of claim 21, wherein said first interference comprises blood cells, and said removing comprises centrifuging or filtering the portion of the first fluid sample.

23. The method of claim 21, wherein said analysis system comprises a spectroscope, and said second interference comprises a substance having spectroscopic features that overlap spectroscopic features of the analyte.

24. The method of claim 23, wherein the first fluid sample comprises blood, and the portion of the first fluid sample comprises plasma.

25. The method of claim 23, wherein the analyte comprises at least one of glucose, blood urea nitrogen, or lactate.

26. The method of claim 23, wherein the interference comprises at least one of sodium bicarbonate and urea.

27. The method of claim 21, further comprising:
   drawing, via the fluid handling system, the second fluid sample from the patient, the second fluid sample comprising blood or a component of blood;

transporting, via the fluid handling system, a portion of the second fluid sample to the analysis system; and correcting for an interference to a determination of a concentration of said analyte in the portion of the second fluid sample, wherein the fluid handling system is configured to remain in fluid communication with the fluid source in the patient during said drawing, said transporting, and said correcting of the second fluid sample.

* * * * *